US008999728B2

(12) United States Patent
Nazareth et al.

(10) Patent No.: US 8,999,728 B2
(45) Date of Patent: Apr. 7, 2015

(54) DIAGNOSTIC DETECTION DEVICE

(75) Inventors: Albert R. Nazareth, Mercerville, NJ (US); Shang Li, Princeton Junction, NJ (US)

(73) Assignee: Church & Dwight Co., Inc., Princeton, NJ (US)

( * ) Notice: Subject to any disclaimer, the term of this patent is extended or adjusted under 35 U.S.C. 154(b) by 693 days.

(21) Appl. No.: 13/332,571

(22) Filed: Dec. 21, 2011

(65) Prior Publication Data

US 2013/0164858 A1 Jun. 27, 2013

(51) Int. Cl.
*G01N 33/53* (2006.01)
*G01N 33/558* (2006.01)
*G01N 33/76* (2006.01)
*G01N 33/68* (2006.01)

(52) U.S. Cl.
CPC .............. *G01N 33/558* (2013.01); *G01N 33/76* (2013.01); *G01N 33/689* (2013.01); *Y10S 435/97* (2013.01); *Y10S 435/973* (2013.01); *Y10S 436/81* (2013.01); *Y10S 436/814* (2013.01)

(58) Field of Classification Search
CPC ............ G01N 33/76; G01N 2333/471; G01N 2333/59; G01N 33/558
See application file for complete search history.

(56) References Cited

U.S. PATENT DOCUMENTS

| 5,602,040 | A | 2/1997 | May et al. |
| 5,622,871 | A | 4/1997 | May et al. |
| 5,656,503 | A | 8/1997 | May et al. |
| 5,714,389 | A | 2/1998 | Charlton et al. |
| 5,739,041 | A | 4/1998 | Nazareth et al. |
| 5,989,921 | A | 11/1999 | Charlton et al. |
| 6,046,057 | A | 4/2000 | Nazareth et al. |
| 6,187,598 | B1 | 2/2001 | May et al. |
| 6,228,660 | B1 | 5/2001 | May et al. |
| 6,277,650 | B1 | 8/2001 | Nazareth et al. |
| 6,319,676 | B1 | 11/2001 | Nazareth et al. |
| 6,352,862 | B1 | 3/2002 | Davis et al. |
| 6,485,982 | B1 | 11/2002 | Charlton |
| 6,500,627 | B1 * | 12/2002 | O'Connor et al. ........... 435/7.92 |
| 6,767,714 | B2 | 7/2004 | Nazareth et al. |
| 6,927,034 | B2 * | 8/2005 | O'Connor et al. ........... 435/7.92 |
| 7,045,342 | B2 | 5/2006 | Nazareth et al. |
| 7,198,954 | B1 * | 4/2007 | O'Connor et al. .............. 436/65 |
| 7,238,537 | B2 | 7/2007 | Davis et al. |
| 7,285,391 | B2 * | 10/2007 | O'Connor et al. ............. 435/7.1 |

(Continued)

FOREIGN PATENT DOCUMENTS

WO 9009592 8/1990

OTHER PUBLICATIONS

A. Krichevsky et al. Development and characterization of a new, highly specific antibody to the human chorionic gonadotropin-β fragment. Endocrinology 1991, vol. 128, No. 3, 1255-1264.

(Continued)

*Primary Examiner* — Chris L Chin
(74) *Attorney, Agent, or Firm* — Ryan Cagle

(57) ABSTRACT

The invention comprises a device for detecting an analyte in a liquid sample deposited on a first portion of the device for transport to a second portion of the device that is in fluid contact with the first portion. In specific embodiments, the device is a pregnancy test device, which detects human chorionic gonadotropin (hCG) as an indicator of pregnancy. Devices with improved clinical sensitivity are provided which are capable of detecting all clinically relevant hCG isoforms.

29 Claims, 4 Drawing Sheets

(56) References Cited

U.S. PATENT DOCUMENTS

| | | |
|---|---|---|
| 7,384,796 B2 | 6/2008 | Davis et al. |
| 7,399,636 B2 * | 7/2008 | O'Connor et al. ............... 436/65 |
| 7,407,813 B2 | 8/2008 | Davis et al. |
| 7,629,178 B2 | 12/2009 | Davis et al. |
| 7,776,618 B2 | 8/2010 | Nazareth et al. |
| 7,790,403 B2 * | 9/2010 | O'Connor et al. ............. 435/7.1 |
| 7,977,104 B2 * | 7/2011 | O'Connor et al. ............... 436/65 |
| 7,993,858 B2 * | 8/2011 | O'Connor et al. ............ 435/7.21 |
| 8,163,508 B2 * | 4/2012 | O'Connor et al. ............ 435/7.21 |
| 8,278,109 B2 * | 10/2012 | Nazareth et al. ................. 436/65 |
| 8,420,339 B2 * | 4/2013 | O'Connor et al. ............ 435/7.21 |
| 8,431,405 B2 * | 4/2013 | Nazareth et al. ................. 436/65 |
| 8,691,585 B2 * | 4/2014 | O'Connor et al. ............ 436/65 |
| 8,802,381 B2 * | 8/2014 | O'Connor et al. ............ 435/7.21 |
| 2006/0040405 A1 | 2/2006 | Charlton et al. |
| 2010/0311188 A1 | 12/2010 | Nazareth et al. |
| 2011/0201122 A1 | 8/2011 | Nazareth et al. |

OTHER PUBLICATIONS

R. McChesney et al. Intact hCG, free hCG β subunit and hCG β core fragment: longitudinal patterns in urine during early pregnancy. Human Reproduction 2005, vol. 20 No. 4, 928-935.

S.F. de Medeiros et al. Urinary concentrations of beta core fragment of hCG throughout pregnancy. Obstet. Gynecol 1992, vol. 80, No. 2, 223-230.

In-house report by W. Stewart. Determination of the sensitivity of pregnancy testing devices to hCG and hCG related molecules when present in isolation or in combination. Nov. 2008.

M.A. Cervinski and A. M. Gronowski. Reproductive-endocrine point-of-care testing: current status and limitations. Clim Chem Lab Med 2010, 48 (7), 935-942.

* cited by examiner

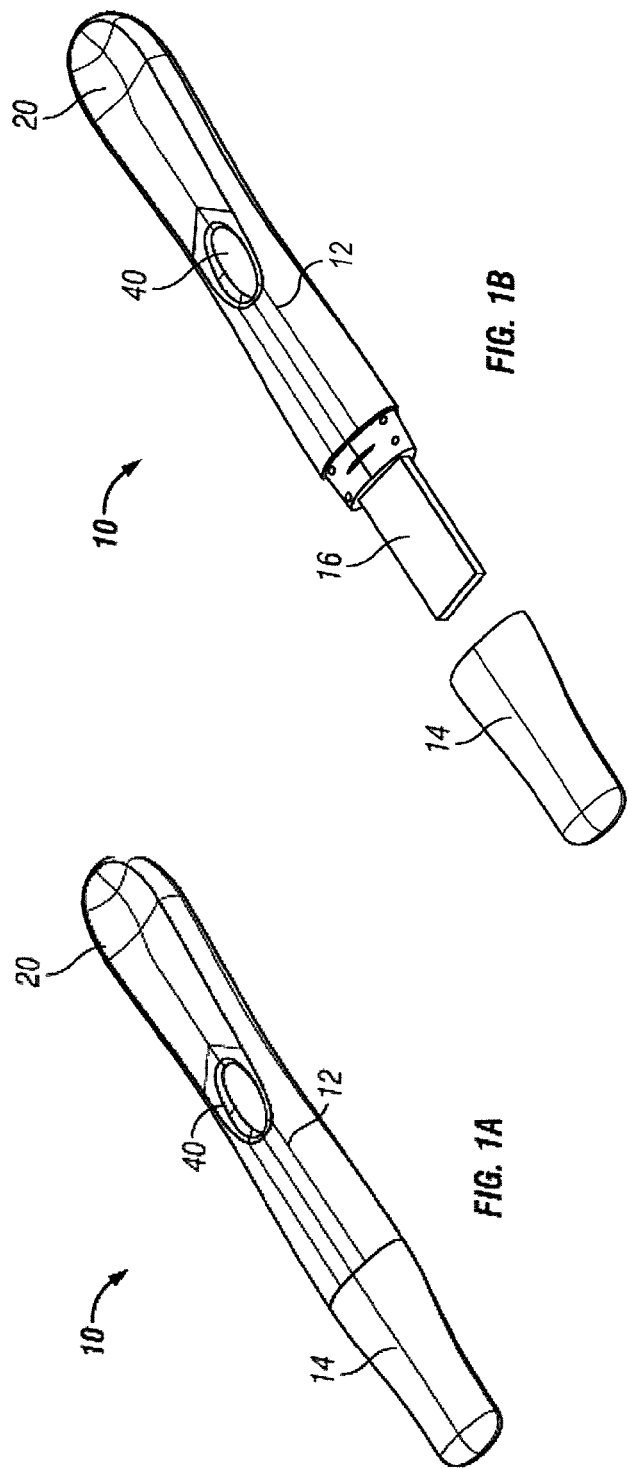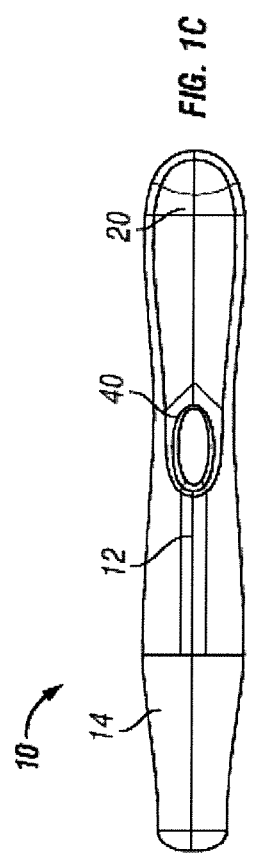

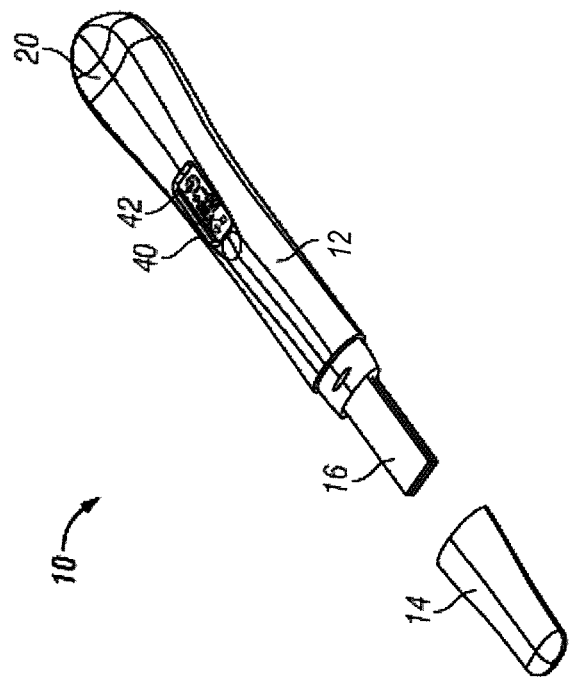
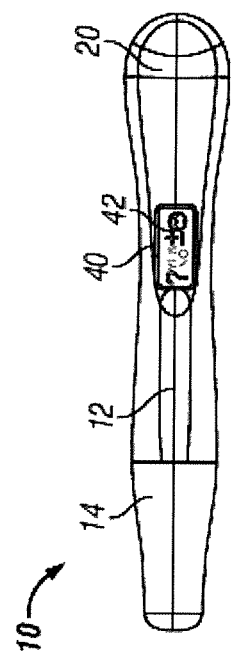
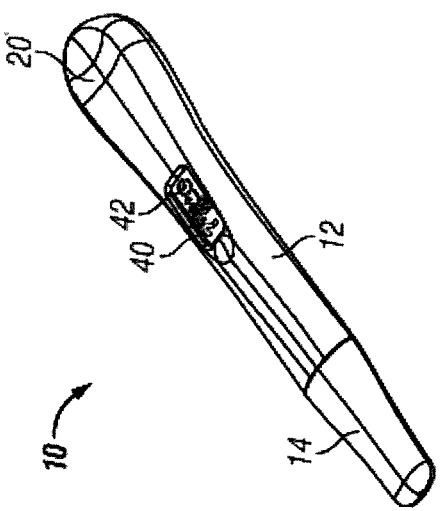
FIG. 2B
FIG. 2C
FIG. 2A

DIAGNOSTIC DETECTION DEVICE

FIELD OF THE INVENTION

The invention relates to devices and methods for detecting human chorionic gonadotropin (hCG) as an indicator of pregnancy. More particularly, the devices can provide improved analytical and clinical sensitivity by detecting all clinically relevant hCG isoforms.

BACKGROUND

Human chorionic gonadotropin (hCG) is a glycoprotein hormone produced during pregnancy. The hCG hormone is produced by the developing embryo soon after fertilization and later by syncytiotrophoblast cells in the developing placenta, and its primary function is to maintain the production of progesterone by the corpus luteum in early pregnancy. The hCG hormone is a member of the glycoprotein hormone family (GPH) that also includes luteinizing hormone (LH), follicle stimulating hormone (FSH), and thyroid stimulating hormone (TSH). All members of the GPH family are heterodimers that consist of an alpha and beta subunit. The alpha subunit is conserved across the GPHs, while the beta subunit of hCG is unique, although there remains about 80% homology across the beta subunits within the GPH family. In addition to conferring differentiation, the beta subunit also grants each heterodimer its unique biological activity and receptor specificity.

Intact hCG, which is also known as regular hCG, has a molecular weight of around 37 kDa and is composed of 244 amino acids. The alpha subunit contains 92 amino acids and the beta subunit contains 145 amino acids. Intact hCG is generally present at varying levels throughout pregnancy, has been noted to be the predominant form of hCG in later stages of pregnancy, and has previously been believed to have the most biological relevance throughout all stages of pregnancy. Multiple variants of hCG that exhibit independent functions are currently recognized and one of these is hyperglycosylated hCG (hCG-H) which is predominantly produced in early pregnancy. A variety of dissociation and degradation products of hCG are found in blood and urine and these include, among others, nicked hyperglycosylated hCG, nicked hCG, free hCG beta subunit (hCG-β), nicked free hCG beta subunit, nicked hyperglycosylated hCG free beta subunit, and hCG beta core fragment (hCG-βcf). See de Medeiros et al., *Human Reproduction Update* 15(1): 69-95 (2009) and Birken et al., *Endocrinology* 123: 572-583 (1988), which are incorporated herein by reference.

In early pregnancy urine, the levels of hCG and its dissociation and degradation products, collectively referred to as hCG isoforms or variants, vary greatly from day to day and from subject to subject. Most pregnancy tests have been developed to preferentially detect intact hCG or to detect some combination of hCG, hCG-H, and hCG-β.

One distinct degradation product of hCG is the hCG beta core fragment (hCG-βcf), which is a fragment of hCG-β, has a molecular weight of about 14 kDa, and contains 73 amino acids in its protein core. The hCG-βcf isoform is now recognized to be a predominant form of hCG present in urine from about seven weeks of pregnancy. See de Medeiros et al., *Obstet. Gynecol,* 80(2): 223-230 (1992), which is incorporated herein by reference. It has been noted that high levels of hCG-βcf can cause false negative results in urine-based pregnancy tests. For more information, see Diwan, *Med. Lab. Observer* pg. 18-20 (February 2011); Cervinski et al., *Clin. Chem. Lab. Med.* 48(7): 935-942 (2010); Gronowski et al., *Clin. Chem.* 55(7): 1389-1394 (2009), which are incorporated herein by reference. Previous and current pregnancy tests, however, do not detect this isoform or have only limited detection capability for this isoform in urine samples.

Accurate and rapid detection of low levels of various hCG isoforms is desirable to confirm pregnancy early after conception has occurred. Further, it is desirable to minimize incidences of false negative results. Accordingly, it would be beneficial to develop a pregnancy test to detect multiple relevant forms of hCG (e.g., all clinically relevant forms of hCG) to increase the reliability and accuracy of pregnancy detection, particularly in early pregnancy.

SUMMARY OF THE INVENTION

The present invention provides systems and methods for identifying the presence in liquid samples of pregnancy indicators, and can be particularly useful for pregnancy detection. In particular, the invention provides systems and methods that allow for the detection of all clinically relevant isoforms of hCG that may be present in a liquid sample. For example, the invention may provide devices that are capable of detecting hCG-βcf in addition to one or more other hCG isoforms. Such systems and methods may provide enhanced sensitivity (e.g., increased provision of positive results early in pregnancy when levels of hCG present in the urine of a subject are low and often previously inconclusive). Such systems and methods may provide enhanced clinical sensitivity (e.g., a lower likelihood of false negative pregnancy test results), which can be evidenced by enhanced analytical sensitivity.

In certain aspects, the invention provides a device for detecting human chorionic gonadotropin (hCG) isoforms in a liquid sample, wherein the device comprises a substrate comprising: i) a first antibody that recognizes all clinically relevant hCG isoforms; ii) a second antibody that is specific for an epitope unique to the hCG beta core fragment (hCG-βcf) isoform or that is specific for an epitope common to both hCG-βcf and hCG beta subunit (hCG-β); and iii) a third antibody that binds multiple hCG isoforms but not the hCG-βcf isoform. In specific embodiments, one of the following conditions can be met: a) the first antibody can be conjugated with a detectable label; or b) both of the second antibody and the third antibody can be conjugated with one or more detectable labels. In certain embodiments, a device is provided, wherein the substrate comprises a release medium formed of a first material and a capture medium formed of a second, different material.

In some embodiments, a device is provided, wherein the second and third antibodies are immobilized at one or more capture sites located on the capture medium. The second and third antibodies, for example, can be mixed, and the mixture of antibodies can be immobilized at the capture site. In such embodiments, the first antibody can be deposited on the release medium. The first antibody can, in certain embodiments, be conjugated with a detectable label.

In some embodiments, a device is provided, wherein the first antibody is immobilized at a capture site located on the capture medium. In such embodiments, the second and third antibodies can be, for example, deposited on the release medium. The second and third antibodies can be deposited on separate regions of the release medium or can be mixed, and the mixture of antibodies can be deposited on the release medium. In certain embodiments, the second and third antibodies may be conjugated with one or more detectable labels.

In certain embodiments, a device is provided wherein the capture medium includes a capture component immobilized at a capture site, the capture component comprising avidin or an equivalent thereof. In such devices, the first antibody, second antibody, and third antibody may be deposited on the release medium. For example, the first antibody, the second antibody, and third antibody can be deposited on separate regions on the release medium or in some embodiments, the first antibody is deposited on a first region on the release medium, and the second and third antibodies are mixed and the mixture of antibodies is deposited on a second, separate region on the release medium. In devices utilizing a capture component comprising avidin, one or more of the antibodies preferably can be conjugated with biotin (i.e., biotinylated). Further, one or more of the antibodies preferably can be conjugated with a detectable label.

For example, in some embodiments, the second and third antibodies are both biotinylated. In such embodiments, the first antibody may optionally be conjugated with a detectable label. In other embodiments, the first antibody is biotinylated and both of the second and third antibodies may optionally be conjugated with one or more detectable labels. The form of the avidin can vary; for example, the avidin can comprise monomeric or polymeric avidin. In certain embodiments, the avidin can comprise streptavidin.

In certain embodiments, one, two, or three of the first antibody, the second antibody, and the third antibody are monoclonal antibodies. In preferred embodiments, all of the first, second, and third antibodies are monoclonal antibodies. The detectable label or labels, where present, can vary. In some embodiments, the detectable label comprises a colored particle. For example, in certain embodiments, the colored particle is a colloidal gold particle (i.e., a gold sol). The first, second, and third antibodies and their specificities for certain hCG isoforms can vary. For example, in certain embodiments of the invention, the second antibody is specific for an epitope unique to hCG-βcf or specific to an epitope that is common to both hCG-βcf and hCG-β.

In another aspect of the present invention is provided a method for detecting human chorionic gonadotropin (hCG) isoforms in a liquid sample. In certain embodiments, the method comprises applying a liquid sample to a device for detecting human chorionic gonadotropin (hCG) isoforms in a liquid sample. The device can be a device as described above, which comprises a substrate comprising: i) a first antibody that recognizes all clinically relevant hCG isoforms; ii) a second antibody that is specific for an epitope unique to hCG-βcf or that is specific for an epitope common to both hCG-βcf and hCG-β; and iii) a third antibody that binds multiple hCG isoforms but not the hCG-βcf isoform. As above, the first antibody can be conjugated with a detectable label, or both of the second antibody and the third antibody can be conjugated with one or more detectable labels. Applying the liquid sample is generally done such that any hCG isoform in the liquid sample flows with the liquid across the substrate so as to contact the antibodies so as to form a sandwich complex comprising relevant hCG isoforms. After applying the liquid sample, the method may further comprise determining the presence of one or more of the hCG isoforms in the liquid sample by inspection of a capture site on the substrate, wherein the presence of the hCG isoforms is indicated by the presence of a detectable signal (e.g., at the capture site) caused by the presence of the sandwich complexes at the capture site. For example, the detectable signal can comprise color development (or other visually identifiable means) such as may provide a visual signal. Further, the detectable signal may be a signal that is electronically analyzed so as to provide a digital output, giving the user the results in a digital form.

In a further aspect of the present invention is provided a method for increasing clinical sensitivity by detecting the presence of multiple pregnancy indicators in a liquid sample. For example, such method can comprise applying a liquid sample to a device as described above, such that various hCG isoforms in the liquid sample flow with the liquid across the substrate so as to contact the antibodies and form sandwich complexes comprising relevant hCG isoforms. The method further can comprise determining the presence of one or more of the hCG isoforms in the liquid sample by inspection of a capture site on the substrate, wherein the presence of the hCG is indicated by a detectable signal resulting from the presence of the sandwich complexes at the capture site. The device beneficially can provide enhanced clinical sensitivity for detecting a pregnancy as compared to devices that do not include the antibody that is specific for the hCG-βcf isoform. The clinical sensitivity for detecting a pregnancy can vary, and in certain embodiments, the clinical sensitivity can be significantly better than the clinical sensitivity of devices that do not include the antibody that is specific for the hCG-βcf isoform. In certain embodiments, the clinical sensitivity of the device incorporating the antibody specific for hCG-βcf can exceed the clinical sensitivity of a similar device that does not include the antibody that is specific for hCG-βcf when measured 6 days, 5 days, or 4 days before the expected menstrual period. For example, the clinical sensitivity of the device may be about 5% or greater, about 10% or greater, or about 15% or greater on these days. In certain embodiments, the device may be about 5% or greater on days 6, 5, and 4 before the expected menstrual period when compared to similar device without the antibody for hCG-βcf isoform. For example, in one specific embodiment, the clinical sensitivity of the device incorporating the antibody specific for hCG-fβcf is around 14%, around 20%, and around 10% greater on days 6, 5 and 4, respectively, before the expected menstrual period when compared to similar device without the antibody that is specific for the hCG-βcf isoform.

BRIEF DESCRIPTION OF THE DRAWINGS

The present invention is particularly described in reference to the following figures; however, such figures are provided to illustrate only preferred embodiments of the invention, and the invention is not intended to be limited thereto.

FIGS. 1A and 1B show a perspective view, and FIG. 1C shows a top view, of an analog detection device;

FIGS. 2A and 2B show a perspective view, and FIG. 2C shows a top view, of a digital detection device;

DETAILED DESCRIPTION OF THE INVENTION

Figure 3:
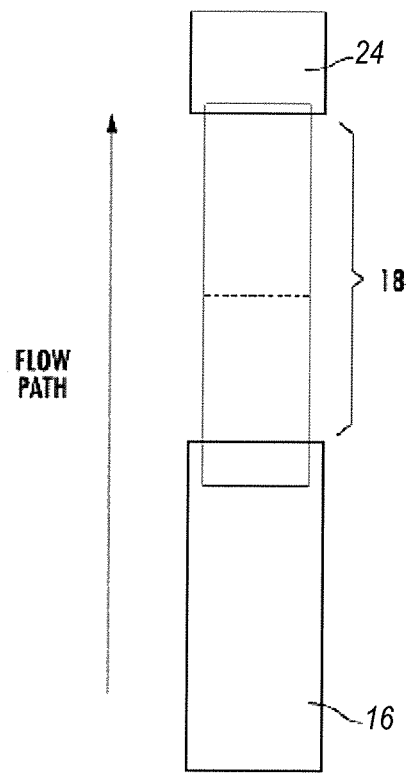
FIG. 3 shows a top view of lateral flow test components comprising a reservoir absorbent material, a biphasic substrate, and a sample receiving member outside of a casing.

The present inventions now will be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements. As used in the specification, and in the appended claims, the singular forms "a," "an," and "the" include plural referents unless the context clearly dictates otherwise.

In one aspect, the present invention provides a pregnancy test device, such as an over-the-counter (OTC) or point of care (POC) test device, for detecting human chorionic gonadotropin (hCG). The device generally includes a proximal portion (e.g., a sample receiving member) in fluid communication with a distal portion (e.g., a reservoir). The proximal and distal portions may be interconnected by a substrate material, which itself may form all or part of the proximal and/or distal portion of the device. A liquid sample (e.g., urine) can be directly or indirectly deposited on the proximal portion of the device for transport to the distal portion. Preferably, the liquid sample flows across the substrate so as to contact one or more antibodies attached to or otherwise deposited on the substrate. The antibodies can be designed and/or chosen to recognize specific hCG isoforms or groups of specific hCG isoforms. In various embodiments of the present invention, devices are provided which include an antibody that recognizes (i.e., binds with) multiple hCG isoforms (e.g., "all clinically relevant hCG isoforms") and two or more antibodies that are specific to epitopes of various hCG isoforms.

As used herein, "all clinically relevant hCG isoforms" refers to the various forms of hCG that can be useful in making a clinical evaluation of pregnancy in a subject when such forms of hCG are present in a liquid sample obtained from the subject. The term can encompass component subunits of hCG and degradation products of hCG and component subunits thereof. Specifically, the term may encompass intact hCG, nicked hCG, hyperglycosylated hCG (hCG-H), hCG-β, nicked hCG beta subunit, and hCG-fβcf. Other antibodies used in the invention can recognize a subset of the above-defined group of all clinically relevant hCG isoforms and/or a single isoform from the above-defined group. Such subsets may expressly exclude one or more of the above-defined clinically relevant isoforms of hCG. In some embodiments, a device is provided that comprises: 1) an antibody that recognizes all clinically relevant hCG isoforms; 2) an antibody that is specific for an epitope unique to hCG-βcf or that is specific to an epitope common to both hCG-βcf and hCG-β; and 3) an antibody that binds to multiple hCG isoforms but not the hCG-βcf isoform.

As used herein, "antibody" refers to a polypeptide substantially encoded by an immunoglobulin gene or immunoglobulin genes, or fragments thereof, which may specifically recognize and bind an antigen. The recognized immunoglobulin genes include the kappa, lambda, alpha, gamma, delta, epsilon, and mu constant region genes, as well as the immunoglobulin variable region genes. Antibodies include fragments, such as Fab', F(ab)$_2$, Fabc, and Fv fragments. The term "antibody," as used herein, also includes antibody fragments either produced by the modification of whole antibodies or those synthesized de novo using recombinant DNA methodologies, and further includes "humanized" antibodies made by now conventional techniques. Although polyclonal antibodies can be used according to the present invention, antibodies are preferably monoclonal antibodies.

An antibody "specifically binds to," "is selectively reactive with," or "is selectively immunoreactive with" a protein or epitope thereof when the antibody functions in a binding reaction with the protein without significantly binding with other proteins. In order for the antibody to bind to a protein, the protein should contact the antibody. Accordingly, contacting a sample suspected of containing an antigen of interest with an antibody to the antigen will permit the antibody to bind the antigen. The binding of the antibody to the protein permits determination of the presence of the protein in a sample in the presence of a heterogeneous population of proteins and other agents. Thus, under designated immunoassay conditions, the specified antibodies selectively bind to a particular protein and do not significantly bind to other proteins present in the sample (e.g., they bind with a differential discrimination of about 90% or greater or about 95% or greater). Specific binding to a protein under such conditions requires an antibody that is selected for specificity or selectivity for a particular protein. Several methods for determining whether or not a peptide is immunoreactive with an antibody are known in the art.

As used herein a "moderate to high affinity" antibody or binding member thereof comprises an antibody or binding member that can bind with a particular antigen within a relatively short incubation time. Likewise, an antibody or binding member thereof "exhibits a moderate to high affinity" for a particular antigen should be understood as requiring a relatively short sample incubation time. For instance, an antibody or binding member exhibits "moderate to high affinity" at equilibrium ("KA") that is greater than $1e^9$ (e.g., about $1e^{10}$, about $1e^{11}$, or about $1e^{12}$) or preferably at least $1e^{10}$ (e.g., $1e^{10}$ to $1e^{12}$). In certain embodiments, KA values at equilibrium of about $1e^9$ to about $1e^{10}$ can be deemed as exhibiting a moderate affinity, while KA values at equilibrium of greater than $1e^{10}$ can be deemed as exhibiting a high affinity. At equilibrium, KA values of $1e^9$ or less can be deemed as exhibiting a low affinity. Such KA values can be experimentally determined using any suitable method known in the art. Specifically, such KA values can be determined by analysis with a Biacore (GE Healthcare) instrument.

As used herein, an antibody "preferentially binds to," "is preferentially reactive with," or "is preferentially immunoreactive with" hCG-fβcf if the antibody exhibits greater than about 50% differential discrimination of hCG-βcf over intact hCG. In certain embodiments, an antibody "preferentially binds to," "is preferentially reactive with" or "is preferentially immunoreactive with" hCG-βcf if the antibody exhibits about 60% or greater, about 70% or greater, about 80 or greater, or about 90% or greater differential discrimination of hCG-βcf over intact hCG. In some embodiments, the antibody exhibits about 50% or greater, about 60% or greater, about 70% or greater, about 80% or greater, or about 90% or greater differential discrimination of hCG-fβcf over all other hCG isoforms. However, in some embodiments, an antibody that "preferentially binds to," "is preferentially reactive with" or "is preferentially immunoreactive with" hCG-fβcf may be specific for an epitope of hCG-βcf that is common to hCG-β and therefore, the antibody may also recognize and bind to hCG-β. Thus, even though such antibodies may bind and may bind significantly to hCG-β, these antibodies are still considered to "preferentially bind to," and be "preferentially reactive with" or "preferentially immunoreactive with" hCG-fβcf and thus are intended to be encompassed within the present invention.

In some embodiments, this antibody is a moderate to high affinity antibody that selectively or preferentially recognizes and binds hCG-fβcf. Preferably, such moderate to high affinity antibodies exhibit limited to minimal binding to intact hCG or other hCG related molecules that may be present in a liquid sample. However, in certain examples, as noted, the moderate to high affinity antibodies may also exhibit binding to hCG-β. For example, mouse and sheep monoclonal antibodies have been developed to target epitopes of hCG-βcf. In certain embodiments, a monoclonal antibody that is specific to both hCG-β and hCG-fβcf, with low cross-reactivity to intact hCG and no cross-reactivity to LH, FSH, and TSH can be used. Such antibodies that can be used to target an epitope within hCG-βcf include, but are not limited to, Ab11382 from Abcam®; ANT-147 from Prospec, GTX11382 from Genetex, 20-783-71060 from GenWay Biotech, Inc., NB 100-62639 from Novus Biologicals, 128-10090-1 from Raybiotech, Inc., SM2159P from Acris Antibodies GmbH, and 13-2172 from American Research Products. Such antibodies may be commercially available. See, for example, Krichevsky et al., *Endocrinology* 128(3): 1255-1264 (1991), which is incorporated herein by reference.

The antibody that recognizes multiple hCG isoforms but not hCG-βcf can be any anti hCG antibody that meets this requirement (i.e., recognizes two or more isoforms from the defined list of clinically relevant isoforms but does not recognize hCG-βcf).

The antibody that recognizes all clinically relevant hCG isoforms is preferably an antibody that recognizes all isoforms and may, in some embodiments, show limited to no selectivity for particular hCG isoforms. Reference herein to antibodies that recognize all clinically relevant hCG isoforms relates to antibodies that recognize intact hCG, nicked hCG, hyperglycosylated hCG (hCG-H), hCG-β, nicked hCG beta subunit, and hCG-βcf. See, for example, U.S. Patent Application Publication No. 2011/0201122 to Nazareth et al., which is incorporated herein by reference.

One or more of the antibodies described herein may function as a "capture antibody." A capture antibody should be understood as an antibody, such as a monoclonal or polyclonal antibody, attached to a substrate directly or indirectly, such as a solid substrate. The capture antibody is most preferably a monoclonal antibody. The capture antibody can include at least one binding member that may specifically or preferentially bind a particular, distinct epitope of an antigen, such as hCG-fβcf or intact hCG or may recognize multiple hCG isoforms (e.g., all clinically relevant isoforms or all clinically relevant isoforms except hCG-βcf).

Embodiments of the present invention preferably make use of a conjugate comprising one or more antibodies bound to detectable label components (which can be colored particles, such as a metal sol or colloid particles, and preferably gold or latex beads or soluble dyes). Typically, one or more of the at least three antibodies used in the devices of the present invention (e.g., one or two) are labeled. Any detectable label recognized in the art as being useful in various assays could be used in the present invention. In particular, the detectable label component can include compositions detectable by reflective, spectroscopic, photochemical, biochemical, immunochemical, or chemical means. As such, the label component produces a detectable signal. For instance, suitable labels include soluble dyes, fluorescent dyes, chemiluminescent compounds, radioisotopes, electron-dense reagents, enzymes, colored particles, or dioxigenin. The label component can generate a measurable signal, such as radioactivity, fluorescent light, color, or enzyme activity, which can be used to identify and quantify the amount of label bound to a capture site. Thus, the label component can also represent the presence or absence of a particular antigen bound thereto, as well as a relative amount of the antigen (e.g., relative to a known standard or threshold standard). In certain embodiments, the label component can comprise gold colloid particles with a mean particle size of about 20 nm to about 100 nm prior to formation of the labeled conjugate. For example, the mean particle size may be about 35 nm to about 80 nm. In certain embodiments, the mean particle size can range from about 50 nm to about 100 nm. Selection of label components and sizes thereof are discussed in detail in U.S. Pat. No. 7,776,618 to Nazareth et al., which is incorporated herein by reference. Thus, the mean particle size of colloidal gold particles used according to the invention may have a size of about 30 nm to about 50 nm. Alternately, particles having a size of about 60 nm to about 80 nm may be used. Combinations of particles sizes also may be used. For further detail regarding various test parameters, see for example U.S. Pat. Nos. 6,319,676; 6,767,714; and 7,045,342 to Nazareth et al., which are incorporated herein by reference.

In certain embodiments, the present invention provides devices that make use of a sandwich technique. In such techniques, the antibody or antibodies used in the detection comprise a binding member or site which binds to an epitope on the analyte for detection. The antibody preferably has a label component bound thereto to provide a labeled antibody. The labeled antibody reacts with the analyte to form a complex in the liquid sample. The analyte, which is bound with the labeled antibody or antibodies, reacts with one or more capture antibodies to form a "sandwich," comprising the capture antibody, analyte (or antigen), and the labeled antibody. Each sandwich complex thus produced comprises three components: one capture antibody, one antigen, and one labeled antibody. The makeup of each sandwich complex, however, can vary depending upon the particular labeled antibody (and thus the particular antigen) included therein. In the same test, there will be multiple different types of sandwiches produced. The sandwich complexes are progressively produced as the test liquid with the analyte therein continuously moves along the substrate of the device. As more and more analyte/labeled antibody complex is immobilized in sandwich form with the capture antibody or antibodies at the capture site, the label components aggregate and become detectable. As described herein, "becoming detectable" relates to the accumulation of sandwich complexes at the capture site, which can be detected in various ways, such as by visual inspection of, for example, color development at the capture site or by a digital readout resulting from the electronic analysis of the aggregate at the capture site as further described herein. Further detail regarding the production of digital signals is provided, for example, in U.S. Pat. No. 7,214,542 to Hutchinson; U.S. Pat. No. 7,220,597 to Zin et al.; and U.S. Pat. No. 7,499,170 to Sasaki et al., which are incorporated herein by reference.

Various embodiments of labeled and capture antibodies are encompassed by the present invention. The labeled antibody may, in certain cases, comprise an antibody that recognizes all clinically relevant hCG isoforms, and the capture antibodies can comprise: 1) an antibody that is specific for an epitope unique to hCG-βcf or that is specific to an epitope common to both hCG-βcf and hCG-β; and 2) an antibody that binds to multiple hCG isoforms but not hCG-βcf. In certain embodiments, the labeled antibodies may comprise: 1) an antibody that is specific for an epitope unique to hCG-βcf or specific to an epitope common to both hCG-βcf and hCG-β; and 2) an antibody that binds to multiple hCG isoforms but not hCG-βcf, and the capture antibody can comprise an antibody that recognizes all clinically relevant hCG isoforms.

Embodiments of the invention can include one or more standards or internal controls that allow for determination of whether signal development (e.g., color development) is a true indication of the presence or absence of hCG analyte in the sample or is simply an artifact, such as caused by nonspecific sorption. For example, in one embodiment employing the sandwich technique, the standard consists of a negative control site, preferably disposed adjacent to the test site (i.e., the capture site), and visible through a second window proximate the first. The negative control site preferably is prepared identically to the test site, except immobilization of the capture antibody is omitted. Therefore, although the conjugate will reach the negative control site, it will aggregate due only to non-specific binding. If the test site is not appreciably more intense in color than the negative control site, the assay is considered negative. In certain embodiments, the device can include a positive control. Thus, when exploiting the sandwich technique for example, a positive control site may have an authentic sample of the analyte for detection immobilized at the positive control site. If no color develops at this control site, the assay is considered inconclusive.

In yet another embodiment, the substrate comprises a control site disposed thereon and located downstream of the capture site. The control site has immobilized thereon at least one capture antibody (e.g., a protein). The primary function of the control site is to capture and immobilize labeled antibody which has not been captured at the capture site. According to various embodiments, the control site can include polyclonal antisera specific for the labeled antibody immobilized thereon. Indication of the presence of the label component at the control site indicates proper functioning of the test, irrespective of the presence or absence of analyte in the sample. Preferably, both the capture and control sites are visible through the window of the casing.

In a preferred embodiment, the inventive device incorporates a biphasic chromatographic medium (substrate/test strip) which enhances the speed and sensitivity of the assay. Generally, a biphasic substrate element useful according to the invention comprises a release medium joined to a capture medium located downstream of the release medium. The release and capture media preferably comprise two different materials or phases having different specific characteristics. The two phases are joined together to form a single liquid path such that a solvent front can travel unimpeded from the proximal (upstream) end of the release medium (which can be defined as a proximal portion of the biphasic medium) to the distal (downstream) end of the capture medium (which can be defined as a distal portion of the biphasic medium). A sample receiving member is generally provided at the proximal end of the biphasic substrate and a reservoir of sorbent material is generally located beyond the biphasic substrate.

Reagents for detecting, labeling, and capturing an analyte of interest are disposed on the release and capture media. In certain embodiments, one or more labeled conjugates are located on the release medium and each includes a binding member (e.g., antibody) that may be reactive with a particular site (sometimes referred to as a "first epitope," "second epitope," etc.) on the analyte of interest. As noted, the labeled conjugate may, in some embodiments, comprise an antibody that recognizes all clinically relevant hCG isoforms. In other embodiments, the labeled conjugates may comprise an antibody that is specific for an epitope unique to hCG-βcf or that is common to both hCG-βcf and hCG-β and/or an antibody that binds to multiple hCG isoforms but not the hCG-βcf isoform. The labeled conjugates further comprise a detectable marker (or label), preferably colloidal gold. Where more than one labeled conjugate is present (i.e., where two or more different labeled antibodies are provided), the detectable marker can be the same or different. For example, in certain embodiments, a first antibody can be labeled with a first marker (e.g., a gold sol having a mean particle size of 20-50 nm), and a second antibody can be labeled with a second marker (e.g., a gold sol having a mean particle size of 60-100 nm). In certain preferred embodiments, labeled conjugates (i.e., conjugates comprising different antibodies) are labeled using the same detectable marker.

The release medium can be formed from a substance which allows for release of reagents deposited therein. Reagents "deposited thereon" may comprise reagents that are releasably (i.e., not permanently) bound to the release medium. In certain embodiments, the release medium comprises a bibulous, hydrophilic material, such as absorbent materials. Preferred materials for use as a release medium include, but are not limited to, cotton linter, cellulosic materials, or materials made of cellulose together with a polymeric fibrous material, such as polyamide or rayon fibers, and glass fiber material. The primary function of the release medium is first to support and to subsequently release and transport various immunological components of the assay, such as a labeled conjugate and/or a capturable conjugate, both of which are capable of binding to the analyte of interest. This release and transport occurs during routine operation of the assay. Generally, the release medium can be formed of any material capable of performing the function of holding, releasing, and transporting various immunological parts of the test such as the labeled test component.

Specific, non-limiting examples of materials useful in forming the release medium include: cotton linter paper, such as S&S 903, S&S GB002, and BFC 180 (available from Whatman, Fairfield, N.J.); cellulosic materials, such as Grade 939 made of cellulose with polyamide, Grade 989 made of cellulose blend fiber, and Grade 1278 and Grade 1281 made of cellulose and rayon with polyamide (available from Ahlstrom Corporation, Mt. Holly Springs, Pa.); and glass fiber, such as Lydall borosilicate (available from Lydall, Inc., Rochester, N.H.). The release medium preferably is coated with an aqueous solution containing bovine serum albumin (BSA) and a nonionic surfactant, such as Triton X-100 (available from Rohm & Haas Co., Philadelphia, Pa.) in order to prevent nonspecific binding and facilitate release of the diffusible reagents. A combination of about 3% BSA and about 0.1% Triton X-100 is useful for this purpose.

The capture medium can be formed from a material which permits immobilization of reagents for detection of the presence of analyte in the test fluid. Immobilization of reagents refers to any interaction that results in antibodies or analytes being irreversibly bound to the substrate such that they are not appreciably washed away, e.g., during the course of a single use of the device. The capture medium generally comprises hydrophilic polymeric materials, such as microporous films or membranes, which permit protein reagents to be immobilized directly on the membrane by passive adsorption without the need for chemical or physical fixation. Of course, the use of chemical or physical fixation is not precluded by the invention, and any known method for immobilizing the reagents to the membrane can be used.

Non-limiting examples of materials useful as the capture medium comprise a microporous polymeric film of nitrocellulose, nylon (e.g., nylon 66), or similar materials, or combinations of such materials. Materials for use as the capture medium preferably have a pore size in the range of from about 5 μm to about 20 μm. In specific embodiments, the nitrocellulose membrane may be nitrocellulose alone or a mixed ester of nitrocellulose, such as in combination with an ester of nitric acid and/or other acids. The nitrocellulose membrane preferably is coated or laminated onto a translucent or transparent polymeric film to provide physical support for the membrane.

In a preferred embodiment, a nitrocellulose polymer which has been cast onto a polyester film, such as MYLAR®, is used. Alternatively, a nitrocellulose membrane laminated onto a polyester film also may be used, although other backing materials besides polyester may be used. Pre-laminated or pre-cast sheets useful in the present invention are commercially available, for example, from Millipore Corporation, Bedford, Mass. and Sartorius Corporation, Edgewood, N.Y.

In one embodiment, the release medium and capture medium are joined by overlapping the downstream edge of the release medium over the upstream edge of the capture medium, then adhering the resulting biphasic material to a clear polymer film or opaque sheet, thereby holding the media in place. The overlapping region allows for the efficient and rapid transfer of analyte containing fluid from the release medium to the capture medium.

While the rapid transfer associated with the overlapping region is useful, the manufacturing issues associated with reproducibly generating a small overlapping region, such as necessary with small devices, can be difficult. Therefore, in certain embodiments, the invention also provides a test device having a biphasic design as described herein but wherein the release medium and the capture medium do not overlap but rather are connected by a non-overlapping butt joint. In such embodiments, the fluid front moving along the test strip is transferred from the release medium to the capture medium through bridging the non-overlapping region by capillary action. Beneficially, the butt joining of the phases can maintain the same efficacy of the overlapping of the phases, even after accelerated aging of the devices. Thus, the use of a butt joint simplifies the manufacture of the present test device without any loss of performance in the device.

The diffusible and non-diffusible reagents can be applied to the release and capture media, respectively, by any suitable technique. In one embodiment, the diffusible reagents are applied to the release medium by direct application onto the surface of the medium and dried to form a narrow band.

In one preferred embodiment, the device comprises a casing defining a sample inlet, a test volume, and reservoir volume. Disposed within the casing are a sample receiving member, the biphasic chromatographic substrate(s), and reservoir absorbent. The sample receiving member is preferentially disposed within the casing and extending to the exterior thereof. Located downstream of the sample receiving member is the biphasic chromatographic substrate comprising a release medium and a capture medium joined together to form a single liquid path. The release and capture media can be laminated onto a transparent or opaque plastic film or sheet.

The sample receiving member preferably is a bibulous hydrophilic material which facilitates absorption and transport of a fluid sample to the biphasic chromatographic medium. Such materials may include cellulose acetate, hydrophilic polyester, and other materials having similar properties. Further, a combination of absorbent materials also may be used. Non-limiting examples of useful materials include bonded cellulose acetate, bonded polyolefin, or hydrophilic polyester, such as those materials commercially available from Filtrona Fibertec Company (Colonial Heights, Va.). Other useful materials include absorbent matrices, such as Grade 939, Grade 989, Grade 1278, or Grade 1281, available from Ahlstrom Corporation. The sample receiving member preferably is coated with a buffered solution containing BSA and a nonionic surfactant, such as Triton X-100. The presence of BSA and surfactant minimize non-specific adsorption of the analyte. A concentration of about 1% BSA and about 0.2% surfactant in tris buffer can be effective for this purpose.

By providing a reservoir of sorbent material disposed beyond the chromatographic substrate, a relatively large volume of the test liquid and any analyte it contains can be drawn through the test area to facilitate background clearance and thereby aid sensitivity. The reservoir absorbent generally facilitates capillary action along the chromatographic substrate and absorbs excess liquid contained within the device. The reservoir absorbent preferably compromises absorbent paper made from cotton long linter fibers, such as CF3, CF4, CF5, or 470 (available from Whatman) or cellulosic materials, such as Grade 3 mM (available from Whatman) and Grade 320 (available from Alhstrom).

In using a device according to various embodiments of the invention, the proximal portion of the biphasic substrate is contacted with the liquid sample being analyzed, wherein the liquid sample can be collected either directly or through the sample receiving member comprising the sample collector. The casing of the device may be configured to permit direct contact with a body fluid or as a dipstick for dipping in a container of body fluid or other test solution. The liquid sample travels impelled by surface effects such as by capillary action along the liquid path formed by the substrate. More specifically, the test sample passes through the biphasic chromatographic substrate and into reactive contact with the test site (e.g., the capture site), and optionally one or more control sites. Preferably, at least the test site is visible to a user, such as through one or more windows in the device's exterior casing. In a preferred embodiment, the labeled binding member or members recognizing the analyte is/are disposed in preserved form on the release medium in the flow path within the device.

Various types of devices are provided according to the present invention. Certain devices (i.e., traditional lateral flow devices), allow for detection of the analyte by directly binding the analyte. In such embodiments, at least one of the release medium and the capture medium includes an antibody that exhibits a moderate to high affinity for an epitope unique to the hCG-fβcf isoform or for an epitope common to both hCG-fβcf and hCG-β isoforms and an antibody that binds multiple hCG isoforms but not the hCG-fβcf isoform. The other of the release medium and the capture medium comprises an antibody that recognizes all clinically relevant isoforms. Other devices (i.e., affinity-based devices), rely on indirect binding to detect the analyte. Both conventional lateral flow and affinity-based types of devices are described in further detail below.

A traditional lateral flow device generally comprises one or more labeled antibodies releasably attached to a substrate that may recognize (i.e., bind to) an analyte to be detected and one or more additional antibodies (generally unlabeled) that are immobilized on the downstream, capture portion of the substrate. In use, a liquid sample passes through the inlet and into the interior of a device, where it comes into contact with the substrate. If the analyte of interest is present in the sample, it reacts with the one or more labeled antibodies which are releasably attached to the release medium. The liquid sample, now comprising analyte-labeled antibody conjugates, wicks up the release medium and forms a sandwich complex with one or more capture antibodies immobilized on the capture medium (defining a capture site or test site). As the sample front passes across the capture site, a complex is formed comprising the analyte, labeled antibody, and the capture antibody. This "sandwich" complex can be detected by noting the presence of the label at the capture site.

FIGS. 1A-C illustrate an embodiment of exemplary device 10. FIG. 1A illustrates a perspective view of the device with the cap intact, while FIG. 1B illustrates a perspective view of the device with the cap removed. FIG. 1C illustrates a top view of the device with the cap intact. The device comprises an outer, molded casing 12 which defines a hollow, elongate enclosure. The casing 12 includes a detection opening 40, comprising a window through which a test site (and control site, if applicable) is visible. Casing 12 is configured to provide a recessed portion 20 shaped to permit users to place their thumb into the recessed portion and their forefinger on the bottom of the casing to securely hold the device 10. A central section on the top of the casing 12 defines the centrally located window 40 which permits a user to observe test results on a portion of a lateral flow test strip inside the casing 12, details of which are described further herein. The surface of the test strip in the area of the window 40 may be covered with a clear polymer layer that prevents contamination during use.

The device 10 further includes a sample receiving member 16, functioning as a test liquid inlet onto which a liquid sample can be applied to the test strip. Sample receiving member 16 can be covered by a removable cap 14. Sample receiving member 16 is positioned so that part of the sample receiving member is received in the casing enclosure and part of the sample receiving member extends from the end of the casing enclosure. In this embodiment, a test liquid inlet 16 is external to the casing 12 and may be covered by the cap 14 except when in use. Providing the test liquid inlet 16 external to the casing 12 allows for ease of application of the test liquid to the device 10, such as by placing the test liquid inlet 16 in the path of a urine stream or in a container holding the test liquid. The cap 14 is re-attachable (such as by "snap-fitting" onto a lip extending from casing 12) and can be replaced after application of the test liquid to avoid contamination of the sample while the test is proceeding. In this embodiment, the capture sites and control sites visible to the user through the window 40 provide a color or reflectivity change which can be viewed by a user to detect the presence of an analyte and proper functioning of the device.

FIGS. 2A-C illustrate another embodiment of an exemplary device 10. FIG. 2A illustrates a perspective view of the device with the cap intact, while FIG. 2B illustrates a perspective view of the device with the cap removed. FIG. 2C illustrates a top view of the device with the cap intact. The device also comprises an outer, molded casing 12 which defines a hollow, elongate enclosure, and shares many similarities with the device illustrated in FIGS. 1A-1C. Casing 12 is configured to provide a recessed portion 20 shaped to permit users to place their thumb into the recessed portion and their forefinger on the bottom of the casing to securely hold the device 10. A central section on the top of the casing 12 defines a centrally located window 40 which permits a user to observe test results. Inside the casing 12 is a lateral flow test strip and electronic components, details of which will be described further below. Casing 12 defines a sample receiving member 16 onto which a liquid sample can be applied to the test strip in the device. A removable cap 14 can be secured to one end of the casing enclosure over the sample receiving member 16. Sample receiving member 16 is positioned so that part of the sample receiving member is received in the casing enclosure and part of the sample receiving member extends from the end of the casing enclosure. In this embodiment, color or reflectivity changes are sensed electronically, and the results are presented to a user on a display 42. The display 42 may render various icons or messages to a user, such as test results, device status, or error messages. The display 42 may be color or monochrome. In one embodiment, the display 42 is a liquid crystal display (LCD).

FIG. 3 illustrates a preferred embodiment of the lateral flow test components. The components comprise a sample receiving member 16, biphasic chromatographic substrate 18, and reservoir absorbent material 24. When the device is placed in contact with a liquid sample, the liquid is transported by capillary action, wicking, or simple wetting along the flow path downstream through sample receiving member 16, along chromatographic substrate 18, and into reservoir absorbent material 24, generally as depicted by the arrow. Sample receiving member 16 may also serve as a filter which can remove particulate matter and interfering factors from a sample. The sample receiving member 16 preferably is a bibulous hydrophilic material which facilitates absorption and transport of a fluid sample to the biphasic chromatographic substrate 18. Such materials may include cellulose acetate, hydrophilic polyester, or other materials having similar properties. A combination of absorbent materials also may be used. Preferred materials include bonded cellulose acetate, bonded polyolefin or hydrophilic polyester, such as those materials commercially available from American Filtrona Company (Richmond, Va.). Other preferred materials include absorbent papers such as Grade 989 or Grade 939 made of cellulose with polyamide and Grade 1281 made of cellulose and rayon with polyamide, available from Filtertek, Inc. The sample receiving member preferably is coated with a buffered solution containing BSA and a nonionic surfactant, such as Triton X-100. The presence of BSA and surfactant can minimize non-specific absorption of the analyte. For example, a concentration of about 1% BSA and about 0.2% surfactant in tris buffer can be effective for this purpose. As noted above, a filtration means which limits the introduction to the test site of contaminants from the sample may also be included.

According to certain embodiments of the present invention which provide lateral flow devices, it is preferable that at least one of the labeled antibody and the capture antibody includes a binding member that exhibits a preferential specificity to hCG-βcf (which may or may not bind an epitope of hCG-β). For example, in certain embodiments, the release medium comprises antibodies comprising: 1) a first labeled antibody specific for an epitope unique to hCG-βcf or specific for an epitope common to both hCG-βcf and hCG-β; and 2) a second labeled antibody that binds multiple hCG isoforms but not the hCG-βcf isoform. In such embodiments, the capture medium may comprise a capture antibody that recognizes all clinically relevant hCG isoforms. The lateral flow process described above will thus result in the labeled complexes accumulating at the capture site (i.e., sandwich complexes of the first labeled antibody, hCG isoform, and the capture antibody and sandwich complexes of the second labeled antibody, hCG isoform, and the capture antibody).

In other embodiments, the release medium comprises a labeled antibody that recognizes all clinically relevant hCG isoforms. In such embodiments, the capture medium may comprise: 1) a first antibody specific for an epitope unique to hCG-βcf or specific to an epitope common to both hCG-βcf and hCG-β; and 2) a second antibody that binds multiple hCG isoforms but not the hCG-fβcf isoform. Again, the lateral flow process described above will result in the labeled complexes accumulating at the capture site (i.e., sandwich complexes of the labeled antibody, hCG isoform, and the first capture antibody and sandwich complexes of the labeled antibody, hCG isoform, and the second capture antibody).

The presence of the analyte (e.g. hCG-βcf or other isoform) is determined by detecting (e.g., visual observation) the presence of the sandwich complex by means of the detectable marker at the capture site. If no analyte is present in the sample, the complex does not form and no detectable marker will be present at the capture site. If a control site is present, the free labeled binding member will accumulate at the control site.

In one specific embodiment, the labeled antibody comprises an anti-hCG antibody that recognizes all clinically relevant hCG isoforms and which is labeled with gold particles. In this embodiment, two capture antibodies are provided, comprising both an antibody that binds to all clinically relevant isoforms but not hCG-βcf and an antibody specific for hCG-βcf. In another embodiment, the labeled antibody comprises the anti-hCG antibody which recognizes all clinically relevant isoforms, which is labeled with gold particles, and the two capture antibodies comprise an antibody that binds to all clinically relevant isoforms but not hCG-βcf and an antibody specific to an epitope that is common to both hCG-βcf and hCG-β. In other embodiments, the capture antibody comprises an anti-hCG antibody, which recognizes all clinically relevant hCG isoforms and the labeled antibody comprises a labeled antibody that binds to all clinically relevant isoforms but not hCG-βcf and a labeled antibody specific for hCG-βcf. In a further embodiment, the capture antibody comprises an anti-hCG antibody that recognizes all clinically relevant hCG isoforms and the labeled antibody comprises a labeled antibody that binds to all clinically relevant isoforms but not hCG-βcf and a labeled antibody specific to an epitope that is common to both hCG-βcf and hCG-β.

Certain embodiments according to the present invention are based on the use of capturable affinity agents (e.g., biotin) present on one or more binding members (i.e., antibodies). In such embodiments, one or more capturable conjugates can be located on the release medium, which conjugates comprise an antibody with a binding agent (i.e., affinity agent) reactive with a particular site (sometimes referred to as an epitope) on the analyte of interest. The capturable conjugate also comprises one member of an affinity pair and is capable of forming a complex with the labeled binding member and the analyte. The labeled conjugate and the capturable conjugate both are releasably bound to the release medium such that when the solvent front created by the liquid sample being analyzed passes through the release medium, the labeled conjugate and the capturable conjugate both become solubilized by the liquid and flow with the solvent along the liquid path. In operation, if any analyte is present in the liquid sample, it reacts with the labeled conjugate and with the capturable conjugate as the front advances along the liquid path to form a diffusible sandwich complex which is transported by capillary action. Thus, by the time the solvent front reaches the capture medium section of the biphasic material, the capturable sandwich complex has formed. The capture medium preferably comprises a capture site for capturing the sandwich complexes, the capture site having immobilized thereon a capture component (e.g., monomeric or polymeric avidin) that reacts with the affinity agent/binding agent.

Such tests rely on binding between affinity pairs (e.g., avidin and biotin), wherein one member of the affinity pair (e.g., biotin) is present on a capturable conjugate (and subsequently on any diffusible sandwich complex formed therefrom) and the other member of the affinity pair (e.g., avidin) is present on the capture medium section of the substrate. This binding between biotin and avidin can provide an indication of a positive result (i.e., the presence of one or more analytes of interest). Upon diffusion into the capture medium, the diffusible sandwich complex becomes concentrated by the interaction of the capture affinity member with the capturable affinity moiety, yielding a detectable signal. The affinity member is immobilized, preferably by simple adsorption, at the capture site, and does not substantially advance with the solvent front.

In use, if the analyte of interest is present in the liquid sample, it passes through the inlet and the interior of the device where it sequentially reacts with the labeled antibody and the antibody with the affinity agent, thereby forming a capturable sandwich complex. The capturable sandwich complex then reacts with the immobilized capture component at the capture site, the capture component being specific for the affinity agent on the capturable conjugate. This process results in the labeled complex accumulating at the capture site. The presence of the analyte is determined by observing the presence of the detectable marker at the capture site. If no analyte is present in the sample, the capturable sandwich complex does not form and no detectable marker will be present at the capture site. If a control site is present, the unbound complex or the free labeled binding member will accumulate at the control site.

Figure 4:
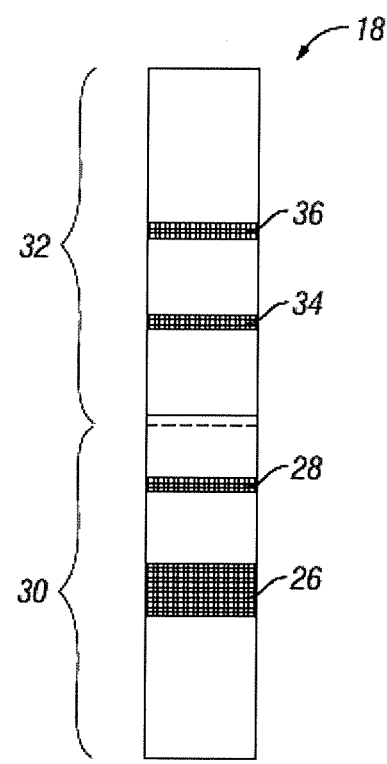
FIG. 4 shows a top view of an embodiment of a biphasic substrate for use in a test device according to the invention.

Referring to FIG. 4, there is provided an example of a substrate according to the invention for use in an affinity pair type embodiment. FIG. 4 illustrates an exemplary biphasic chromatographic substrate 18, comprising a release medium 30 and a capture medium 32 joined together to form a single liquid path. In certain embodiments, use of a biphasic chromatographic medium may enhance the speed and sensitivity of an assay, such as those described in U.S. Pat. Nos. 6,319,676; 6,767,714; and 7,045,342, which are incorporated herein by reference, including without limitation for the purpose of describing biphasic chromatographic media. Methods for manufacturing biphasic chromatographic media are also described in detail in U.S. Pat. No. 5,846,835, the disclosure of which is incorporated herein by reference in its entirety.

In some embodiments, the release medium comprises a bibulous, hydrophilic material, such as absorbent paper. Other materials useful in forming the release medium include, for example, cotton linter paper such as S&S 903 and S&S GB002 (available from Schleicher and Schuell, Inc., Keene, N.H.), and BFC 180 (available from Whatman, Fairfield, N.J.); and glass fiber such as Lydall borosilicate (available from Lydall, Inc., Rochester, N.H.). The release medium is also preferably coated with a buffered solution containing BSA and a nonionic surfactant, such as Triton X-100. The presence of BSA and surfactant can minimize non-specific binding and facilitate release of the diffusible reagents. For example, a concentration of about 3% BSA and about 0.1% surfactant can be used.

In some embodiments, the capture medium 32 comprises a hydrophilic polymeric material, preferably a nitrocellulose or nylon membrane. Preferred materials for use as a capture medium are microporous films or membranes which permit protein reagents to be immobilized directly on the membrane by passive adsorption without need for chemical or physical fixation. For this purpose, membranes of nitrocellulose, nylon 66 or similar materials are preferred, most preferably having a pore size in the range of from about 5um to about 20 µm. Nitrocellulose membranes may be nitrocellulose alone or a mixed ester of nitrocellulose.

Both the release medium and the capture medium may be laminated onto a polyester film such as MYLAR® or other polymer backing to form a solid phase support. For example, the release and capture media may be laminated onto 5 mil clear PET precoated with an adhesive (available from Adhesives Research).

Upon lamination, the release medium is positioned on top of the capture medium, allowing a small region of overlap between the two media to aid in fluid transfer. This biphasic material containing the assay reagents can be cut into test strips (e.g., as shown in FIG. 4) that can be assembled into a test device (e.g., as shown in FIGS. 1 & 2). Briefly, the release medium and capture medium can be positioned such that they overlap slightly, with an adhesive disposed on the back of each (i.e., the side opposite that which will receive the reagents). The adhesive may be any pressure sensitive or hot melt adhesive which does not fill the pores of the release or capture medium, thereby permitting unimpeded flow of the fluid front through the media. Commercially available adhesives, such as those from Adhesives Research Corp. or Lohmann Precision Die Cutting, LLC, can be used. In a preferred embodiment, the adhesive is disposed on a clear polymer backing. The overlapped release and capture media are then passed through the laminating rollers of a laminating machine together with the backed adhesive, forming a laminate of the capture and release media, the adhesive and the polymer backing. The resulting laminated biphasic substrate is then ready to receive the reagents, which are deposited as continuous stripes onto the top of the substrate. Once the reagents have been deposited and dried, if necessary, the substrate is cut into the desired size.

The diffusible and non-diffusible reagents can be applied to the release and capture media, respectively, by any suitable technique. In one embodiment, the diffusible antibody reagents are applied to the release medium by direct application onto the surface of the medium and dried to form a narrow band. The non-diffusible reagents preferably are applied to the capture medium by passive adsorption. The horizontal double line represents the interface between the release medium 30 and the capture medium 32. As previously noted, this interface can be in the form of an overlapping relationship. Alternatively, the release medium 30 can be butted up to the capture medium 32.

Releasably deposited on release medium 30 is a band 26 of dehydrated labeled conjugate binding member, such as an antibody-metal sol specific to a first epitope of the analyte. In one embodiment, the labeled conjugate binding member is in dehydrated form. Metal sols and other types of colored particles useful as marker substances in immunoassay procedures are known to one of skill in the art, such as those in U.S. Pat. No. 4,313,734, which is incorporated herein by reference, including without limitation for the purpose of describing colored particles. Details and engineering principles involved in the synthesis of colored particle conjugates are also known to one of skill in the art, such as those described in Horisberger (Evaluation of Colloidal Gold as a Cytochromic Marker for Transmission and Scanning Electron Microscopy, Biol. Cellulaire, 36, 253-258 (1979)); Leuvering et al. ("Sol Particle Immunoassay", J. Immunoassay 1 (1): 77-91 (1980)), and Frens ("Controlled Nucleation for the Regulation of the Particle Size in Monodisperse Gold Suspensions", Nature, Physical Science, 241: 20-22 (1973)), which are incorporated herein by reference in their entireties.

As the liquid sample moves past band 26, the labeled binding member becomes entrained in the liquid, reconstituted (in the case of a dehydrated binding member), and reacts with or binds to an analyte present in the liquid sample. Disposed downstream of the labeled binding member is a band 28 of preferably dehydrated capturable component. The capturable component comprises a binding member such as an antibody which binds to a second epitope of the analyte. The capturable component also becomes entrained in the liquid sample as it advances along substrate 18. These two antibodies may be conventionally derived from the same species, such as mouse antibodies. The capturable component antibody is preferably biotinylated.

The labeled conjugate and capturable component may be disposed in preserved form, e.g., air dried or freeze-dried, on the release medium 30. Analytes passing through the device contact the labeled conjugate and capturable component, forming a sandwich complex with the complex ultimately being captured by reagents immobilized on the capture medium as described below.

Immobilized on capture medium 32 are, respectively, capture site 34 and optional control site 36. In FIG. 4, the control and capture sites are illustrated as being disposed serially along the flow path. Alternatively, the control and capture site or sites may be disposed side by side, perpendicular to each other, or in other spatial relationships. Capture site 34 comprises a capture component specific for the affinity agent of the capturable component deposited on the release medium. Control site 36 comprises immobilized antisera or an antibody specific for the labeled conjugate. For example, when the capturable affinity member is biotin, the capture component may be avidin. Of course, any such complementary system of components could be used in place of avidin and biotin.

When present, control site 36 comprises immobilized antisera, antibody specific for the labeled conjugate, or a protein binder such as Protein A or Protein G capable of binding the labeled binding member. For example, in some embodiments, the control line 36 has been formed with monoclonal or polyclonal secondary antibodies specific to the antibodies used at line 26 such as goat anti-mouse antibodies. Polyclonal antisera and monoclonal antibodies or fractions thereof having specific binding properties and affinity for antigenic substances for use with the devices described herein are known to one of skill in the art, and/or can be produced from stable cell lines using cell fusion and screening techniques known to one of skill in the art. The literature provides protocols for producing and immobilizing proteins, such as Laboratory Techniques in Biochemistry and Molecular Biology (Tijssen, Vol. 15), Practice and Theory of Enzyme immunoassays (chapter 13), The Immobilization of Immunoreactants on Solid Phases (pp. 297-328), and references cited therein, which are incorporated herein by reference in their entireties. This binding agent can be used to capture labeled binding members which are not captured at the upstream capture site. When used, the presence of the detectable marker at the control site indicates that the assay has operated properly.

The device may further comprise a reservoir absorbent material 24 disposed downstream of the biphasic chromatographic substrate 18 and in fluid communication therewith. By providing a reservoir of sorbent material disposed beyond the biphasic chromatographic substrate, a relatively large volume of a test liquid containing analytes can be drawn through the test area to facilitate background clearance and thereby aid sensitivity. The reservoir absorbent material preferably comprises a hydrophilic material which may be the same as the upstream sample receiving material, although any absorbent material may suffice. Another purpose of the reservoir absorbent material is to facilitate capillary action along the biphasic chromatographic substrate and to absorb excess liquid contained within the device. The reservoir absorbent material preferably compromises absorbent paper made from cotton long linter fibers, such as S&S 300, S&S 470 and S&S 900 (available from Schleicher & Schuell, Inc.) or cellulosic materials, such as Grade 3 mM (available from Whatman) and Grade 320 (available from Alhstrom).

Figure 5:
FIG. 5 shows a side view of the test components of FIG. 3.

FIG. 5 illustrates a side view of the test strip components. As shown, sample receiving member 16 is disposed proximate to release medium 30, and overlaps release medium 30 at one end. Release medium 30 in turn overlaps capture medium 32, which is disposed distal to release medium 30. Reservoir absorbent material 24 overlaps the distal end of capture medium 32. These four components together form a single fluid path, and cooperate to cause sample liquid to flow from sample receiving member 16 along release medium 30 and capture medium 32 into reservoir absorbent material 24.

According to certain embodiments of the present invention based on affinity pairing, a device is provided comprising a biphasic substrate wherein the release medium comprises: 1) a first antibody specific for an epitope unique to hCG-fβcf or specific for an epitope common to both hCG-fβcf and hCG-fβ; 2) a second antibody that binds multiple hCG isoforms but not the hCG-βcf isoform; and 3) a third antibody that recognizes all clinically relevant hCG isoforms. In specific embodiments, the first and second antibodies can be labeled, and the third antibody can be functionalized with an affinity agent. In such embodiments, different types of sandwich complexes can be formed; namely, complexes between the first (labeled) antibody, the relevant hCG isoform or isoforms present in the sample, and the third (functionalized) antibody, and complexes between the second (labeled) antibody, the relevant hCG isoform or isoforms present in the sample, and the third (functionalized) antibody. In other embodiments, the third antibody can be labeled, and the first and second antibodies can be functionalized with an affinity agent. In such embodiments, likewise, different types of sandwiches can be formed; namely, complexes between the first (functionalized) antibody, the relevant hCG isoform or isoforms present in the sample, and the third (labeled) antibody, and complexes between the second (functionalized) antibody, the relevant hCG isoform or isoforms present in the sample, and the third (labeled) antibody.

After formation, such sandwich complexes will flow downstream to the capture medium, which comprises a capture site comprising a capture component (e.g., avidin). The affinity agent on the sandwich complexes can facilitate capture by the capture component at the capture site, and the presence of such sandwich complexes at the capture site can be detected by means of the label thereon.

The release medium, according to one embodiment of the present invention, includes labeled conjugates comprising the detectable label and an antibody that is specific for an epitope of hCG-βcf and an antibody that recognizes multiple hCG isoforms but not the hCG-βcf isoform, and a biotinylated capturable component including an antibody that recognizes all clinically relevant hCG isoforms. As such, when a sample includes hCG-βcf, sandwich complexes are formed comprising the labeled conjugate, hCG-βcf, and the biotinylated capturable component. Additional sandwich complexes will be formed comprising the labeled conjugate, other hCG isoform, and the biotinylated capturable component. In such embodiments, the capture medium comprises a capture site having immobilized thereon a capture component comprising avidin.

In an alternative embodiment, according to the present invention, the release medium includes labeled conjugates comprising the detectable label and an antibody that recognizes all clinically relevant hCG isoforms and a biotinylated capturable component including an antibody that is specific for an epitope of hCG-βcf and an antibody that recognizes multiple hCG isoforms but not the hCG-βcf isoform. As such, when a sample includes hCG-βcf, sandwich complexes are formed comprising the labeled conjugate, hCG-βcf, and the biotinylated capturable component. Additional sandwich complexes will be formed comprising the labeled conjugate, other hCG isoforms, and the biotinylated capturable component. In such embodiments, the capture medium comprises a capture site having immobilized thereon a capture component comprising avidin.

The device, according to one embodiment, comprises a biphasic substrate including a release medium formed of a first material and a capture medium in fluid communication with the release medium and formed of a second, different material. The release medium includes a labeled binding conjugate comprising an antibody that is specific for an epitope of hCG-βcf and an antibody that recognizes multiple hCG isoforms but not the hCG-βcf isoform, and a biotinylated capturable component that recognizes all clinically relevant hCG isoforms, such that if hCG-βcf or other hCG isoforms are present in the sample, a sandwich complex is formed comprising the labeled binding conjugate, hCG-βcf or other hCG isoform, and the biotinylated capturable component. In an alternative embodiment, the release medium includes a labeled binding conjugate comprising an antibody having a site that recognizes all clinically relevant hCG isoforms, and biotinylated capturable components, which comprise antibodies that are specific for an epitope of hCG-fβcf and antibodies that recognize multiple hCG isoforms but not the hCG-βcf isoform, such that if hCG-fβcf or other hCG isoforms are present in the sample, a sandwich complex is formed comprising the labeled binding conjugate, hCG-βcf or other hCG isoforms, and the biotinylated capturable component.

Preferably, at least one of the labeled binding conjugate and the biotinylated capturable component includes a binding member that exhibits a moderate to high affinity for hCG-βcf and is selectively or preferentially reactive with hCG-fβcf. The capture medium includes a capture site for capturing the complex, wherein the capture site includes a capture component immobilized thereon. The capture component can comprise avidin. Further, such embodiments can optionally include a control site. In certain embodiments, the control site can comprise either a negative or positive control as discussed earlier.

According to embodiments including avidin as a capture component, the avidin used in the preparation of test devices according to the invention preferably comprises an avidin solution that can be applied to the test device, thereby immobilizing avidin on the substrate. In certain embodiments, the avidin comprises streptavidin. The avidin in the solution can comprise a number of polymeric forms, such as dimeric, trimeric, tetrameric, or the like. While monomeric avidin can be present in the solution, the solution preferably comprises a majority of polymeric avidin, the total content of any monomeric avidin in the solution comprising only a minority of the total content of the solution. In specific embodiments, the avidin solution comprises polymeric avidin in an amount such that the polymeric avidin comprises at least 50% by weight of the avidin solution. Preferably, the solution comprises at least about 55% by weight, at least about 60% by weight, at least about 75% by weight, or at least about 90% by weight of polymeric avidin.

The methods for attaching avidin, either monomeric or polymeric, to the substrate can vary according to the invention. For example, in certain embodiments, the avidin can be attached directly to the substrate. In other embodiments, the avidin can be indirectly attached to the substrate, such as through a natural or synthetic intermediate material. In one specific embodiment, the avidin can be attached to the substrate via a particulate material, such as latex beads. For example, the avidin can be attached to latex beads via passive adsorption or chemical coupling, and the latex-bound avidin can be dispensed onto the substrate by bonding the latex beads thereto. Preferentially, such latex beads have sizes in the range of about 0.1 µm to about 0.5 µm, more preferably about 0.1 µm to about 0.3 µm. In yet another embodiment, the avidin can be conjugated to an intermediate protein, the intermediate protein being bound to the substrate. Non-limiting examples of materials useful as an intermediate protein for attaching avidin to a substrate include immunoglobulins and bovine serum albumin (BSA).

In one specific embodiment according to the invention, the labeled binding conjugate comprises an anti-hCG antibody that recognizes or binds all clinically relevant hCG isoforms and which is labeled with gold particles. In this embodiment, the biotinylated capturable component comprises a biotinylated antibody that binds multiple hCG isoforms but not the hCG-fβcf isoform and a biotinylated antibody specific for hCG-βcf. Alternatively, the biotinylated capturable component comprises a biotinylated antibody that binds multiple hCG isoforms but not the hCG-fβcf isoform and a biotinylated antibody specific to an epitope common to both hCG-βcf and hCG-β. In a further embodiment, the labeled binding conjugate comprises the antibody specific for hCG-βcf and the antibody that binds multiple hCG isoforms but not the hCG-βcf isoform, and the biotinylated capturable component comprises a biotinylated antibody which recognizes or binds all clinically relevant hCG isoforms. In a still further embodiment, the labeled binding conjugate comprises the antibody specific to an epitope common to both hCG-βcf and hCG-β and the antibody that binds multiple hCG isoforms but not the hCG-fβcf isoform, and the biotinylated capturable component comprises a biotinylated antibody which recognizes or binds all clinically relevant hCG isoforms.

Figure 6:
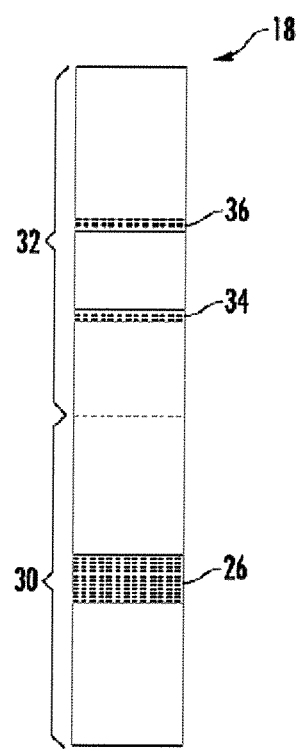
FIG. 6 shows a top view of another embodiment of a biphasic substrate for use in a test device according to the invention.

In certain embodiments utilizing a traditional lateral flow format, as illustrated in FIG. 6, a band 26 of labeled binding member, e.g., an antibody-metal sol, can be releasably disposed on the release medium 30. In one embodiment, the labeled binding member is in dehydrated form. As the liquid sample moves past the band 26, the labeled binding member becomes entrained in the liquid, reconstituted (in the case of a dehydrated binding member), and reacts or binds with a particular analyte or analytes of interest present in the liquid sample. Accordingly, the resulting complex comprising a binding antibody, a label component, and an analyte for identification (e.g., hCG) advances along with the sample front until the reaching the capture site 34. In this particular embodiment, the capture site includes at least one immobilized capture antibody having a binding member which binds to a second epitope of the analyte. Accordingly, a sandwich complex including the desired analyte is formed at the capture site 34. If desired, a control site 36 can include immobilized antisera, antibody, or protein such as Protein A or Protein G capable of binding the labeled binding member.

The device for detecting hCG in a liquid sample, according to one embodiment of the invention, comprises a biphasic substrate. The biphasic substrate can include a release medium formed of a first material and comprising a region including labeled antibodies that include an antibody that is specific for an epitope of hCG-βcf and an antibody that recognizes multiple hCG isoforms but not the hCG-βcf isoform, and a capture medium in fluid communication with the release medium. Preferably, the capture medium can be formed of a second, different material, and include a capture site having an immobilized capture antibody thereon. The immobilized capture antibody can comprise a member that recognizes all clinically relevant hCG isoforms, such that if hCG-βcf and other hCG isoforms are present in the sample, a sandwich complex is formed comprising the labeled antibodies, hCG-βcf or other hCG isoform, and the immobilized capture antibody.

Alternatively, in certain embodiments, the biphasic substrate can include a release medium formed of a first material and comprising a region including a labeled antibody that includes an antibody that recognizes all clinically relevant hCG isoforms, and further can include a capture medium in fluid communication with the release medium. Preferably, the capture medium can be formed of a second, different material, and include a capture site having immobilized capture antibodies thereon. The immobilized capture antibodies can comprise an antibody that is specific for an epitope of hCG-βcf and an antibody that recognizes multiple hCG isoforms but not the hCG-βcf isoform, such that if hCG-βcf and other hCG isoforms are present in the sample, a sandwich complex is formed comprising the labeled antibody, hCG-βcf or other hCG isoform, and the immobilized capture antibodies. The antibody that is specific for an epitope of hCG-βcf and the antibody that recognizes multiple hCG isoforms but not the hCG-βcf isoform can be mixed and striped together or may be striped separately, depending upon the specific embodiment employed. In particular, where the capture antibodies are immobilized on the capture site, the capture antibodies are generally mixed and applied together. In other embodiments, different antibodies may be applied separately.

A side view of one embodiment of the operative portion of the assay materials is schematically illustrated in FIG. 5. As shown, the sample receiving member 16 is disposed proximate the release medium 30, and overlaps the release medium 30 at one end. The release medium 30 in turn overlaps the capture medium 32, which is disposed distal to the release medium 30. Again, the release medium 30 and the capture medium 32 may alternatively be connected via a butt joint rather than being in overlapping connection. The reservoir 24 overlaps the distal portion of the capture medium 32. These four components together form a single fluid path, and they cooperate to cause sample liquid to flow from the sample receiving member 16 along the release medium 30 and the capture medium 32 into the reservoir 24.

The devices of the present invention are not limited by the precise nature of the capture site 34 and the corresponding control site 36, and in fact, the control site 36 may be entirely eliminated if desired. Generally, antibody or other affinity agent can be immobilized at the capture site 34 and the control site 36 using absorption, adsorption, or ionic or covalent coupling, in accordance with methods known per se. The capture medium 32 preferably is selected to bind the capture reagents without the need for chemical coupling. Nitrocellulose and nylon both permit non-chemical binding of the capture component and control reagent. Disposed downstream of the capture medium 32 is the reservoir 24 comprising a relatively large mass of absorbent or superabsorbent material. The purpose of reservoir 24 is generally to ensure that a reasonably large amount of test liquid is drawn across the chromatographic medium. In certain embodiments, the sample receiving member 16 can be omitted, and the release medium 30 can itself act as the sample receiving member. Such embodiments of the assay materials are useful in performing dipstick assays.

The present invention provides test devices having improved overall clinical sensitivity (i.e., the ability to accurately identify positive test results in pregnancy). For example, the invention provides for improved analytical sensitivity by indicating the presence of more hCG isoforms than previously possible while still maintaining the test specificity. This enhancement of analytical sensitivity is provided due to the presence of an antibody that is specific for the hCG-fβcf isoform, which is not traditionally detected in pregnancy test devices. In certain specific embodiments, pregnancy test devices of the present invention provide clinical sensitivity for detecting a pregnancy that is improved in relation to devices that do not include the antibody that is specific for the hCG-fβcf isoform. Such improvement can be relative to days 6, 5 and 4 before the expected menstrual period. The improvement in clinical sensitivity relative to these specific days of the subject's cycle can be about 5% or greater, about 10% or greater, about 15% or greater, or about 20% or greater (e.g., about 10% or greater, about 20% or greater, and about 10% or greater on days 6, 5, and 4, respectively). The improved clinical sensitivity is demonstrated by the Examples.

The test devices of the present invention can be characterized as providing an enhanced analytical sensitivity in that the device can provide a signal gain in comparison to a device that does not include the antibody that is specific for the hCG-fβcf isoform. Such signal gain can be identified when the devices are evaluated using a standard including both intact hCG and the hCG-fβcf isoform. For example, a standard may include about 3.2 mIU/mL to about 25 mIU/mL intact hCG and about 3.2 mIU/mL to about 25 mIU/mL hCG-βcf isoform, or the standard may include about 3.2 mIU/mL to about 12.5 mIU/mL intact hCG and about 3.2 mIU/mL to about 12.5 mIU/mL hCG-fβcf isoform. Standards particularly may include about 3.2 mIU/mL, about 6.3 mIU/mL, or about 12.5 mIU/mL of both intact hCG and the hCG-βcf isoform. For example, the inventive test devices comprising an antibody that is specific for the hCG-fβcf isoform may exhibit signal gains of about 10% or greater, about 20% or greater, about 30% or greater, about 40% or greater, or about 50% or greater as compared with devices without an antibody that is specific for the hCG-fβcf isoform. The signal gains can be characterized as being statistically significant (i.e., having a t-test p-value of less than 0.05) as compared with test devices that do not include an antibody that is specific for the hCG-βcf isoform. The signal gain is beneficial in that better signaling increases the readability of the device by a user. This in turn reduces the incidence of misreading a positive test result as negative. Moreover, such signal gains increases the ability to detect low levels of clinically relevant hCG isoforms in a sample, such as levels that may occur soon after conception, and thus increases the ability to detect pregnancy earlier than other devices that do not detect all clinically relevant hCG isoforms in a sample to provide a definitively readable signal.

In further embodiments, the invention provides various methods for detecting the presence of an analyte (such as hCG) in a liquid sample. The methods of the invention generally comprise the use of a test device as described herein. Typically, the methods of the invention comprise adding a liquid sample to a first portion of an inventive device, allowing the liquid sample to flow across a substrate in the test device (e.g., a biphasic substrate comprising a release medium and a capture medium), and determining the presence of the analyte in the liquid sample by visual inspection (i.e., inspecting the test device to determine if the device indicates a positive result, i.e., accumulation of labeled sandwich complexes at the capture site).

A positive result in a test for detecting hCG in a sample can be shown in various ways in relation to the present devices. In certain embodiments, a positive result is indicated to the user by the presence of color development caused by accumulation of the labeled analyte complexes at a capture site. This accumulation may result in the formation of one or more colored lines or other geometric shape. In other embodiments, a positive result can be indicated to the user by providing a digital output (e.g., a word or symbol) that may read or interpreted by a user (e.g., by indicating "YES" for a positive result or "NO" for a negative result). Such embodiments generally comprise an opto-electronic reader coupled with a software program which can evaluate the intensity/color of the labeled analyte complex, if any, accumulated at the capture site. The opto-electronic reader is equipped to compare the intensity/color against a pre-programmed threshold and, based on the comparison, the device can provide a certain digital output if the intensity/color is above the threshold, and a different digital output if the intensity/color is below the threshold. Still further means for evaluating the test results also are encompassed by the invention.

The present invention will now be described with specific reference to various examples. The following examples are not intended to be limiting of the invention and are rather provided as exemplary embodiments.

EXPERIMENTAL

Having generally described the subject matter, the present invention will now be described with specific reference to various examples. The following examples are not intended to be limiting of the invention and are rather provided as exemplary embodiments.

Example 1

Three comparative pregnancy test devices were prepared. All three devices were based on lateral flow technology that utilizes a biphasic material as described herein. Specifically, the biphasic material was a cellulosic release medium and a nitrocellulose membrane on a solid phase support, both of which were laminated onto a MYLAR backing. Upon lamination, the release medium is positioned on top of the nitrocellulose, allowing a small region of overlap between the two to aid in fluid transfer. In all three devices, the release medium was striped with a first reagent comprising a gold-labeled anti-hCG monoclonal antibody that has a high specificity and affinity to all clinically relevant hCG isoforms.

The release medium was also striped with a second reagent comprising 0.1 mg/mL of a biotin-tagged antibody ("the capture antibody"). In the first device ("known art device"), the capture antibody comprised biotin-tagged monoclonal antibody which recognizes intact hCG, hCG-H, and hCG-β. In the second device ("control device A"), the capture antibody comprised biotin-tagged monoclonal antibody which is highly specific to only hCG-βcf. In the third device ("inventive device A"), the capture antibody comprised a mixture of two types of biotin-tagged antibodies, wherein one antibody comprised biotin-tagged monoclonal antibody which recognizes intact hCG, hCG-H, and hCG-β and the other antibody comprised biotin-tagged monoclonal antibody which is highly specific to only hCG-βcf (striped onto the release medium in a mixture of the two antibodies at a concentration of 0.1 mg/mL each).

In all devices, the nitrocellulose membrane portion of the biphasic material was striped with a third reagent, comprising streptavidin. The striped biphasic material was cut into 8 mm test strips, which allowed the strips to be assembled into test devices. The only difference among the three devices was the composition of the capture antibody stripe on the release medium.

The three devices were evaluated with pooled negative urine spiked with either intact hCG or hCG-fβcf ranging from 3.2 to 100 mIU/mL. Testing was done by dipping the devices in the urine standards for 5 seconds. Visual results were read at 3 minutes after sample application. A commercially available reflectance reader, the BioDot test strip reader, equipped with CCD camera and image analysis software, was used to quantify the color intensity that developed at the test line. Tables 1 and 2 summarize the visual and BioDot results for the three test devices assayed. Individual urine standards were tested in replicates of 3 with the devices.

TABLE 1

Visual and BioDot Analysis of Known Art, Inventive, and Control Devices Tested with Intact hCG Standards

| Intact hCG (mIU/mL) | Known Art Device | | | Inventive Device A | | | Control Device A | | |
|---|---|---|---|---|---|---|---|---|---|
| | Visual | BioDot Avg | STD | Visual | BioDot Avg | STD | Visual | BioDot Avg | STD |
| 0 | 3/3 neg | n/a | | 3/3 neg | n/a | | 3/3 neg | n/a | |
| 3.2 | 3/3 pos | 0.49 | 0.08 | 3/3 pos | 0.68 | 0.05 | 3/3 neg | n/a | |
| 6.3 | 3/3 pos | 1.36 | 0.10 | 3/3 pos | 1.24 | 0.10 | 3/3 neg | n/a | |
| 12.5 | 3/3 pos | 2.32 | 0.33 | 3/3 pos | 2.18 | 0.02 | 3/3 neg | n/a | |
| 25 | 3/3 pos | 3.93 | 0.08 | 3/3 pos | 4.29 | 0.54 | 3/3 neg | n/a | |
| 50 | 3/3 pos | 5.61 | 0.08 | 3/3 pos | 5.89 | 0.39 | 3/3 pos | 0.28 | 0.06 |
| 100 | 3/3 pos | n/a | | 3/3 pos | n/a | | 3/3 pos | 0.46 | 0.03 |

TABLE 2

Visual and BioDot Analysis of Known Art, Inventive, and Control Devices Tested with hCG-βcf Standards

| hCG-βcf (mIU/mL) | Known Art Device | | | Inventive Device A | | | Control Device A | | |
|---|---|---|---|---|---|---|---|---|---|
| | Visual | BioDot Avg | STD | Visual | BioDot Avg | STD | Visual | BioDot Avg | STD |
| 0 | 3/3 neg | n/a | | 3/3 neg | n/a | | 3/3 neg | n/a | |
| 3.2 | 3/3 neg | n/a | | 3/3 pos | 0.26 | 0.02 | 3/3 pos | 0.32 | 0.03 |
| 6.3 | 3/3 neg | n/a | | 3/3 pos | 0.44 | 0.06 | 3/3 pos | 0.46 | 0.06 |
| 12.5 | 3/3 neg | n/a | | 3/3 pos | 0.78 | 0.27 | 3/3 pos | 0.85 | 0.15 |
| 25 | 3/3 neg | n/a | | 3/3 pos | 1.35 | 0.21 | 3/3 pos | 1.40 | 0.34 |
| 50 | 3/3 neg | n/a | | 3/3 pos | 2.26 | 0.14 | 3/3 pos | 1.81 | 0.42 |
| 100 | 3/3 neg | n/a | | 3/3 pos | 3.96 | 1.29 | 3/3 pos | 3.61 | 0.38 |

The data presented above in Tables 1 and 2 shows that the ability of detecting intact hCG or hCG-fβcf with the avidin-biotin assay format is dictated by the specificity and affinity of the biotinylated antibodies used in the system. While the control device did not detect intact hCG below 50 mIU/mL, the inventive and known art devices produced comparable results throughout the assay range and displayed equivalent sensitivity of 3.2 mIU/mL. In contrast, the known art device did not detect the hCG-fβcf urine standards; both the inventive and control devices produced similar responses against the hCG-fβcf urine standards.

The three test devices were then tested with urine standards comprising both intact hCG and hCG-fβcf. Again, testing was done by dipping the devices in standards for 5 seconds and visual results were recorded at 3 minutes after sample application, with BioDot readings taken immediately following visual inspection. Table 3 summarizes the average BioDot readings. The percentages of signal gains listed were calculated by comparing the average BioDot results of the known art device and inventive device. A 2-sample t-test was performed at each hCG level using individual BioDot readings with the known art and inventive devices. In each case, the calculated p value was less than 0.05, showing that the signal gain obtained with the inventive device over the known art device was statistically significant.

The same experiment and statistical analysis were performed to compare the control and inventive devices with these urine standards. Table 4 summarizes the average BioDot readings. While the calculated p value was between 0.05 and 0.1 when tested with the 6.3 mIU standard (showing that the inventive device had a probable signal gain over the control device), the other p values were all less than 0.05, showing that the signal gains obtained with the inventive device over the control device were statistically significant.

TABLE 3

Comparison of Known Art Device and Inventive Device A Tested with Intact hCG and hCG-βcf Standards

| Standard | Known Art Device BioDot G/Den | | Inventive Device A BioDot G/Den | | % Signal Gain Inventive Device A Over Known Art Device | p-value From 2-sample t-test Known Art vs. Inventive Device A | Statistical Significance |
|---|---|---|---|---|---|---|---|
| | Avg | STD | Avg | STD | | | |
| 3.2 mIU hCG | 0.31 | 0.03 | 0.42 | 0.04 | 34% | 0.028 | Significant Signal Gain |
| 3.2 mIU hCG-βcf | | | | | | | |
| 6.3 mIU hCG | 0.47 | 0.03 | 0.71 | 0.06 | 49% | 0.008 | Significant Signal Gain |
| 6.3 mIU hCG-βcf | | | | | | | |

TABLE 3-continued

Comparison of Known Art Device and Inventive Device
A Tested with Intact hCG and hCG-βcf Standards

| Standard | Known Art Device BioDot G/Den Avg | STD | Inventive Device A BioDot G/Den Avg | STD | % Signal Gain Inventive Device A Over Known Art Device | p-value From 2-sample t-test Known Art vs. Inventive Device A | Statistical Significance |
|---|---|---|---|---|---|---|---|
| 12.5 mIU hCG 12.5 mIU hCG-βcf | 0.89 | 0.08 | 1.40 | 0.09 | 56% | 0.005 | Significant Signal Gain |
| 25 mIU hCG 25 mIU hCG-βcf | 1.60 | 0.09 | 2.26 | 0.07 | 41% | 0.002 | Significant Signal Gain |

TABLE 4

Comparison of Control Device and Inventive Device
A Tested with Intact hCG and hCG-βcf Standards

| Standard | Control Device BioDot G/Den Avg | STD | Inventive Device BioDot G/Den Avg | STD | % Signal Gain Inventive over Control Device | p-value from 2-sample t-test Control vs. Inventive | Statistical Significance |
|---|---|---|---|---|---|---|---|
| 3.2 mIU hCG 3.2 mIU hCG-βcf | 0.30 | 0.04 | 0.42 | 0.04 | 42% | 0.029 | Significant Signal Gain |
| 6.3 mIU hCG 6.3 mIU hCG-βcf | 0.44 | 0.11 | 0.71 | 0.06 | 62% | 0.064 | Probable Signal Gain |
| 12.5 mIU hCG 12.5 mIU hCG-βcf | 0.80 | 0.08 | 1.40 | 0.09 | 74% | 0.003 | Significant Signal Gain |
| 25 mIU hCG 25 mIU hCG-βcf | 1.31 | 0.08 | 2.26 | 0.07 | 73% | 0.001 | Significant Signal Gain |

The known art, inventive, and control devices were used to test early pregnancy urine samples from 8 subjects with well characterized conceptive cycles. The clinical urine samples were collected daily from women transitioning from non-pregnant to pregnant. The samples represent EMP-6 to EMP+3 (i.e., six days prior to the subject's expected menstrual period to three days after the subject's expected menstrual period). The samples were stored at −40° C. before use and thawed at room temperature on the day of testing. The hCG levels of these samples were characterized using a Siemens Immulite 1000 Analyzer. The methods that were used to evaluate urine standards containing both intact hCG and hCG-βcf isoforms was applied to this clinical sample testing. Individual urine samples were tested in replicates of 3 with the devices. First, the samples were evaluated using the control device as shown in Table 5.

TABLE 5

Evaluation of Early Pregnancy Urine Samples Containing
Detectable Levels of hCG-βcf from 8 Conceptive Cycles

| | # Samples Tested | # Positive Results | % hCG-βcf Detected with Control Device A |
|---|---|---|---|
| EMP + 3 | 4 | 4 | 100% |
| EMP + 2 | 6 | 6 | 100% |
| EMP + 1 | 7 | 7 | 100% |
| EMP | 7 | 5 | 71% |
| EMP − 1 | 6 | 5 | 83% |
| EMP − 2 | 7 | 4 | 57% |
| EMP − 3 | 6 | 3 | 50% |
| EMP − 4 | 6 | 2 | 33% |
| EMP − 5 | 8 | 1 | 13% |
| EMP − 6 | 6 | 0 | 0% |

As shown in Table 5, the earliest detection of hCG-βcf with the control device was at EMP-5. The percentage of hCG-fβcf detection gradually increases to 100% on EMP+1.

The samples were also evaluated with the known art device and the inventive device. The summary of 2-sample t-test results for these devices is presented in Table 6. Of the 63 clinical early pregnancy urine samples collected from the 8 subjects, 3% of the samples (2 out of the 63 samples) produced significant signal gains (p value<0.05), another 3% of the samples produced probable signal gains (0.05<p value<0.1), and another 3% produced probable signal losses (0.05<p value<0.1) with the inventive device as compared with the known art device. The majority of the samples showed no statistical difference between the results of the known art device and those of the inventive device. This is probably due to low levels of hCG-βcf isoforms present in very early pregnancy urine samples.

TABLE 6

Summary of 2-Sample t-Test Results for Known Art and Inventive
Device A Tested with Early Pregnancy Urine Samples

| p-value from 2-sample t-test | Statistical Significance | # of samples | % of samples |
|---|---|---|---|
| p value < 0.05 (95% confidence) | significant signal gain | 2 | 3% |
| 0.05 < p value < 0.1 (90% confidence) | probable signal gain | 2 | 3% |
| p value < 0.05 (95% confidence) | significant signal loss | 0 | 0% |
| 0.05 < p value < 0.1 (90% confidence) | probable signal loss | 2 | 3% |
| p > 0.10 | no difference | 57 | 90% |

In general, Experiment 1 demonstrates that the inventive device can produce incremental signal gains over the known art device when tested with urine samples containing hCG-βcf. The modified pregnancy test which recognizes all clinically relevant hCG isoforms could thus provide better clinical sensitivity percentages and therefore improved accuracy than the current pregnancy test in early pregnancy urine testing.

Example 2

The known art device, inventive device A, and control device A from Example 1 were compared against a device prepared with a solution of 0.1 mg/mL monoclonal antibody which recognizes intact hCG, hCG-H, and hCG-β and 0.05 mg/mL monoclonal antibody which is highly specific to only hCG-βcf ("inventive device B"). Inventive device A and inventive device B devices produced comparable visual and BioDot results with intact hCG standards throughout the test range (G-100 mIU/mL, as in Example 1). The incorporation of the antibody which is highly specific to only hCG-βcf did not appear to affect the assay sensitivity against intact hCG.

Example 3

Three comparative pregnancy test devices were prepared as in Example 1; however, in place of antibody which is highly specific to only hCG-βcf, monoclonal antibody with specificity to both hCG-βcf and hCG-β was used, giving a known art device, "inventive device C", and a "control device C." The devices were tested in triplicate with negative urine pool, intact hCG, and hCG-βcf urine standards. Samples were allowed to equilibrate to room temperature prior to use. Testing to visually evaluate the response of each device was performed by dipping the devices in the urine standards for 5 seconds and visual results were recorded at 3 minutes. The results are shown in Table 7 and Table 8.

TABLE 7

Visual Results of Known Art Device, Inventive Device C, and
Control Device C Tested with Intact hCG Standards

| Intact hCG (mIU/mL) | Known Art Device | Inventive Device C | Control Device C |
|---|---|---|---|
| NUP | 3/3 neg | 3/3 neg | 3/3 neg |
| 3.2 | 3/3 pos | 3/3 pos | 3/3 neg |
| 6.3 | 3/3 pos | 3/3 pos | 3/3 neg |
| 12.5 | 3/3 pos | 3/3 pos | 3/3 pos |
| 25 | 3/3 pos | 3/3 pos | 3/3 pos |

TABLE 8

Visual Results of Known Art Device, Inventive Device C,
and Control Device C Tested with hCG-βcf Standards

| hCG-βcf (mIU/mL) | Known Art Device | Inventive Device C | Control Device C |
|---|---|---|---|
| NUP | 3/3 neg | 3/3 neg | 3/3 neg |
| 3.2 | 3/3 neg | 3/3 pos | 3/3 pos |
| 6.3 | 3/3 neg | 3/3 pos | 3/3 pos |
| 12.5 | 3/3 neg | 3/3 pos | 3/3 pos |
| 25 | 3/3 neg | 3/3 pos | 3/3 pos |

As summarized in Table 7, both known art and inventive device C produced positive results with hCG urine standards ranging from 3.2 to 25 mIU/mL. Control device C did not display positive results with intact hCG standards at and below 6.3 mIU/mL. Table 8 shows that the known art device did not produce any positive result in this assay; however, both inventive device C and the control device displayed the end point sensitivity of the assay at 3.2 mIU/mL.

Devices prepared in this study were also tested with pooled negative urine and 10 mIU/mL hCG standard that was spiked with 1 IU LH/mL for cross-reactivity evaluation. The results show that LH does not affect the inventive device C or the control device C at the amounts tested and thus, the antibody with specificity to both hCG-fβcf and hCG-β is a practical alternative to the antibody which is highly specific to only hCG-fβcf (Example 1).

Example 4

Two comparative digital pregnancy test devices were prepared. The first device was assembled using standard triphasic test strips. The second (inventive) device was prepared using triphasic test strips that were striped with a premixed solution comprising 0.1 mg/mL biotin-tagged antibody with specificity to both hCG-fβcf and hCG-β and 0.1 mg/mL biotin-tagged monoclonal antibody which recognizes intact hCG, hCG-H, and hCG-β.

Urine samples (523 samples total) from 48 conceptive cycles were obtained from pregnant women. The devices were dipped into each urine sample for 5 seconds and the results were read digitally when displayed on the screen. Results with cycle segments organized according to the day of the EMP and the day of missed period (EMP+1) are tabulated in Table 9. The known art device and inventive device displayed similar sensitivity percentages when tested with clinical samples at day of EMP-7 and before and at days of EMP-3 and after. Notably, an improvement in pregnancy detection (i.e., an increase in clinical sensitivity) was seen with the inventive device as compared with the known art device at EMP-7, EMP-6, EMP-5, and EMP-4. Specifically, the inventive device produced 14%, 20%, and 10% higher clinical sensitivities than the known art device when tested with EMP-6, EMP-5, and EMP-4 samples, respectively and thus showed the potential to provide better early detection of pregnancy.

TABLE 9

Summary of Test Results with Digital Devices Relative to EMP

| | EMP-8 | EMP-7 | EMP-6 | EMP-5 | EMP-4 | EMP-3 | EMP-2 | EMP-1 | EMP | EMP+1 |
|---|---|---|---|---|---|---|---|---|---|---|
| Known Art Digital Device | | | | | | | | | | |
| Positive Results Obtained | 5/40 | 11/47 | 22/48 | 30/47 | 41/48 | 46/48 | 47/48 | 47/47 | 48/48 | 45/45 |
| Percent Pregnancies Detected | 13% | 23% | 46% | 64% | 85% | 96% | 98% | 100% | 100% | 100% |
| Inventive Digital Device | | | | | | | | | | |
| Positive Results Obtained | 5/40 | 13/47 | 25/48 | 36/47 | 45/48 | 46/48 | 47/48 | 47/47 | 48/48 | 45/45 |
| Percent Pregnancies Detected | 13% | 28% | 52% | 77% | 94% | 96% | 98% | 100% | 100% | 100% |
| Percent Improvement Over Known Art Device | 0% | 22% | 14% | 20% | 10% | 0% | 0% | 0% | 0% | 0% |

Many modifications and other embodiments of the inventions set forth herein will come to mind to one skilled in the art to which these inventions pertain having the benefit of the teachings presented in the foregoing descriptions. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A device for detecting human chorionic gonadotropin (hCG) isoforms in a liquid sample, wherein the device comprises a substrate comprising a release medium formed of a first material and a capture medium formed of a second, different material, the substrate having deposited thereon:
   i) a first antibody that recognizes all clinically relevant hCG isoforms;
   ii) a second antibody that is specific for an epitope unique to hCG beta core fragment (hCG-βcf) isoform or specific for an epitope common to both hCG-βcf and hCG beta subunit (hCG-β); and
   iii) a third antibody that binds multiple hCG isoforms but not the hCG-βcf isoform,
   wherein one of the following conditions is met: a) said first antibody is conjugated with a detectable label; or b) both of said second antibody and said third antibody are conjugated with one or more detectable labels; and
   wherein the capture medium of the substrate includes one or more capture sites configured for capture of one or more of the hCG isoforms in the liquid sample.

2. The device of claim 1, wherein the second and third antibodies are immobilized at one or more capture sites located on the capture medium.

3. The device of claim 2, wherein the second and third antibodies are mixed, and the mixture of antibodies is immobilized at the capture site.

4. The device of claim 2, wherein the first antibody is deposited on the release medium.

5. The device of claim 4, wherein the first antibody is conjugated with a detectable label.

6. The device of claim 1, wherein the first antibody is immobilized at a capture site located on the capture medium.

7. The device of claim 6, wherein the second and third antibodies are deposited on the release medium.

8. The device of claim 7, wherein both of the second and third antibodies are conjugated with one or more detectable labels.

9. The device of claim 8, wherein the second antibody and the third antibody are deposited on separate regions of the release medium.

10. The device of claim 8, wherein the second antibody and the third antibody are mixed and the mixture of antibodies is deposited on the release medium.

11. The device of claim 1, wherein the capture medium includes a capture component immobilized at a capture site, the capture component comprising avidin.

12. The device of claim 11, wherein the avidin comprises monomeric or polymeric avidin.

13. The device of claim 11, wherein the first antibody, the second antibody, and the third antibody are deposited on the release medium.

14. The device of claim 13, wherein the first antibody, the second antibody, and the third antibody are deposited on separate regions on the release medium.

15. The device of claim 13, wherein the first antibody is deposited on a first region on the release medium, and wherein the second and third antibodies are mixed and the mixture of antibodies is deposited on a second, separate region on the release medium.

16. The device of claim 13, herein the second and third antibodies are both biotinylated.

17. The device of claim 16, wherein the first antibody is conjugated with a detectable label.

18. The device of claim 13, wherein the first antibody is biotinylated.

19. The device of claim 18, wherein both of the second and the third antibodies are conjugated with one or more detectable labels.

20. The device of claim 1, wherein one, two, or three of the first antibody, the second antibody, and the third antibody are monoclonal antibodies.

21. The device of claim 1, wherein the detectable label comprises a colored particle.

22. The device of claim 21, wherein the colored particle is a colloidal gold particle.

23. The device of claim 1, wherein the second antibody is specific for an epitope common to both hCG-βcf and hCG-β.

24. The device of claim 1, wherein the clinically relevant hCG isoforms comprise intact hCG, nicked hCG, hyperglycosylated hCG (hCG-H), hCG-β, nicked hCG beta subunit, and hCG-βcf.

25. A method for detecting human chorionic gonadotropin (hCG) isoforms in a liquid sample comprising:
   a) applying the liquid sample to a device according to claim 1, such that any hCG isoform in the liquid sample flows with the liquid across the substrate so as to contact the first antibody and one or both of the second antibody and the third antibody so as to form a sandwich complex comprising relevant hCG isoforms; and
   b) determining the presence of one or more of the hCG isoforms in the liquid sample by inspection of a capture site on the substrate, wherein the presence of the hCG isoforms is indicated by the presence of a detectable signal at the capture site caused by the presence of the sandwich complexes at the capture site.

26. A method for increasing sensitivity by detecting the presence of multiple pregnancy indicators in a liquid sample, the method comprising:
   a) applying the liquid sample to a device according to claim 1, such that various hCG isoforms in the liquid sample flow with the liquid across the substrate so as to contact the first antibody and one or both of the second antibody and the third antibody so as to form sandwich complexes comprising relevant hCG isoforms; and
   b) determining the presence of one or more of the hCG isoforms in the liquid sample by inspection of a capture site on the substrate, wherein the presence of the hCG is indicated by the presence of a detectable signal at the capture site caused by the presence of the sandwich complexes at the capture site, wherein the device provides enhanced sensitivity for detecting a pregnancy as compared to devices that do not include the antibody that is specific for the hCG-βcf isoform.

27. The method of claim 26, wherein the enhanced sensitivity comprises clinical sensitivity, wherein the clinical sensitivity for detecting a pregnancy is about 5% or more greater on any of days 6, 5, or 4 before the expected menstrual period than that of a device that does not include the antibody that is specific for the hCG-βcf isoform.

28. The method of claim 26, wherein the enhanced sensitivity comprises enhanced analytical sensitivity, wherein the device provides a signal gain of about 25% or greater in comparison to a device that does not include the antibody that is specific for the hCG-βcf isoform when the devices are evaluated using a standard including about 3.2 mIU to about 25 mIU intact hCG and about 3.2 mIU to about 25 mIU hCG-βcf isoform.

29. The method of claim 28, wherein the signal gain is statistically significant with a t-test p-value of less than 0.05.

* * * * *